US006451602B1

(12) United States Patent
Popoff et al.

(10) Patent No.: US 6,451,602 B1
(45) Date of Patent: Sep. 17, 2002

(54) ANTISENSE MODULATION OF PARP EXPRESSION

(75) Inventors: Ian Popoff, Encinitas; Lex M. Cowsert, Carlsbad, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/517,467

(22) Filed: Mar. 2, 2000

(51) Int. Cl.$^7$ .......................... C12Q 1/68; C07H 21/04; C12N 15/85

(52) U.S. Cl. .......................... 435/375; 435/6; 435/91.1; 435/325; 435/366; 536/23.1; 536/24.31; 536/24.33; 536/24.5

(58) Field of Search .......................... 435/6, 366, 325, 435/375; 536/23.1, 24.5; 514/44

(56) References Cited

U.S. PATENT DOCUMENTS 5,665,710 A * 9/1997 Rahman et al. ................ 514/44

OTHER PUBLICATIONS

W. Michael Flanagan et al., Cellular penetration and antisense activity by a phenoxazine–substituted heptanucleotide, Research, pp. 1–5.*
Andrea D. Branch, A ggod antisense molecule is hard to find, TIBS 23—Feb. 1998, pp. 45–50.*
Douglas W. Green, M.D. et al., Antisense Oligonucleotides: An Evolving Technology for the Modulation of Gene Expression in Human Disease, J. Am. Coll. Surg. vol. 191, No. 1, Jul. 2000, pp. 93–105.*
Kuang–Yu Jen et al., Suppression of Gene Expression by Targeted Disruption of Messenger RNA: Available Options and Current Strategies, Stem Cells 2000; 18: pp. 307–319.*
Sudhir Agrawal et al., Antisense therapeutics: is it as simple as complementary base recognition? Molecular Medicine Today, Feb. 2000, vol. 6, pp. 72–81.*
D.D.F. Ma et al., Synthetic oligonucleotides as therapeutic: the coming of age, Biotechnology Annual Review, vol. 5, pp. 155–196.*
Alkhatib et al., Cloning and expression of cDNA for human poly(ADP–ribose) polymerase [published erratum appears in Proc Natl Acad Sci U S A 1987 Jun;84 (12):4088], *Proc. Natl. Acad. Sci. U. S. A.*, 1987, 84:1224–1228.
Althaus et al., Poly ADP–ribosylation: a DNA break signal mechanism, *Mol. Cell. Biochem.*, 1999, 193:5–11.
Ame et al., PARP, A novel mammalian DNA damage–dependent poly(ADP–ribose) polymerase, *J. Biol. Chem.*, 1999, 274:17860–17868.
Burkart et al., Mice lacking the poly(ADP–ribose) polymerase gene are resistant to pancreatic beta–cell destruction and diabetes development induced by streptozocin, *Nat. Med.*, 1999, 5:314–319.

Cherney et al., cDNA sequence, protein structure, and chromosomal location of the human gene for poly(ADP–ribose) polymerase, *Proc. Natl. Acad. Sci. U. S. A.*, 1987, 84:8370–8374.
D'Amours et al., Poly(ADP–ribosyl)ation reactions in the regulation of nuclear functions, *Biochem. J.*, 1999, 342:249–268.
Duriez et al., Characterization of anti–peptide antibodies directed towards the automodification domain and apoptotic fragment of poly (ADP–ribose) polymerase, *Biochim. Biophys. Acta.*, 1997, 1334:65–72.
Gale, Theory and practice of nicotinamide trials in pre–type 1 diabetes, *J. Pediatr. Endocrinol. Metab.*, 1996, 9:375–379.
Johansson, A human poly(ADP–ribose) polymerase gene family (ADPRTL): cDNA cloning of two novel poly(ADP–ribose) polymerase homologues, *Genomics*, 1999, 57:442–445.
Koedel et al., Oxidative stress in bacterial meningitis, *Brain Pathol.*, 1999, 9:57–67.
Kroger et al., Synergistic effects of thalidomide and poly (ADP–ribose) polymerase inhibition on type II collagen–induced arthritis in mice, *Inflammation*, 1996, 20:203–215.
Kupper et al., Trans–dominant inhibition of poly(ADP–ribosyl)ation potentiates carcinogen induced gene amplification in SV40–transformed Chinese hamster cells, *Cancer Res.*, 1996, 56:2715–2717.
Love, Oxidative stress in brain ischemia, *Brain Pathol.*, 1999, 9:119–131.
Malanga et al., Poly(ADP–ribose) binds to specific domains of p53 and alters its DNA binding functions, *J. Biol. Chem.*, 1998, 273:11839–11843.
Mandir et al., Poly(ADP–ribose) polymerase activation mediates 1–methyl–4–phenyl–1, 2,3,6–tetrahydropyridine (MPTP) –induced parkinsonism, *Proc. Natl. Acad. Sci.U. S. A.*, 1999, 96:5774–5779.
Miesel et al., Modulation of inflammatory arthritis by inhibition of poly(ADP ribose) polymerase, *Inflammation*, 1995, 19:379–387.
Molinete et al., Overproduction of the poly(ADP–ribose) polymerase DNA–binding domain blocks alkylation–induced DNA repair synthesis in mammalian cells, *Embo J.*, 1993, 12:2109–2117.
Oliver et al., Resistance to endotoxic shock as a consequence of defective NF–kappaB activation in poly (ADP–ribose) polymerase–1 deficient mice, *Embo J.*, 1999, 18:4446–4454.

(List continued on next page.)

*Primary Examiner*—John L. LeGuyader
*Assistant Examiner*—M Schmidt
(74) *Attorney, Agent, or Firm*—Licata & TYrrell P.C.

(57) ABSTRACT

Antisense compounds, compositions and methods are provided for modulating the expression of human PARP. The compositions comprise antisense compounds, particularly antisense oligonucleotides, targeted to nucleic acids encoding human PARP. Methods of using these compounds for modulation of human PARP expression and for treatment of diseases associated with expression of human PARP are provided.

26 Claims, No Drawings

OTHER PUBLICATIONS

Pieper et al., Poly (ADP–ribose) polymerase, nitric oxide and cell death, *Trends Pharmacol. Sci.,* 1999, 20:171–181.

Prasad et al., Detection of heterogeneity of apoptotic fragments of poly (ADP–ribose) polymerase in MDA–MB–468 breast cancer cells: two–dimensional gel analysis, *Electrophoresis,* 1999, 20:618–625.

Richardson et al., Effects of PARP inhibition on drug and Fas–induced apoptosis in leukaemic cells, *Adv. Exp. Med. Biol.,* 1999, 457:267–279.

Sheng et al., DNA repair enhancement by a combined supplement of carotenoids, nicotinamide, and zinc, *Cancer Detect. Prev.,* 1998, 22:284–292.

Shiokawa et al., Inhibitors of poly(ADP–ribose) polymerase suppress nuclear fragmentation and apoptotic–body formation during apoptosis in HL–60 cells, *FEBS Lett.,* 1997, 413:99–103.

Simbulan–Rosenthal et al., Regulation of the expression or recruitment of components of the DNA synthesome by poly(ADP–ribose) polymerase, *Biochemistry,* 1998, 37:9363–9370.

Simbulan–Rosenthal et al., Prolongation of the p53 response to DNA strand breaks in cells depleted of PARP by antisense RNA expression, *Biochem. Biophys. Res. Commun.,* 1998, 253:864–868.

Simbulan–Rosenthal et al., The expression of poly(ADP–ribose) polymerase during differentiation– linked DNA replication reveals that it is a component of the multiprotein DNA replication complex, *Biochemistry,* 1996, 35:11622–11633.

Simbulan–Rosenthal et al., Transient poly(ADP–ribosyl)ation of nuclear proteins and role of poly(ADP–ribose) polymerase in the early stages of apoptosis, *J. Biol. Chem.,* 1998, 273:13703–13712.

Simbulan–Rosenthal et al., Involvement of PARP and poly-(ADP–ribosyl)ation in the early stages of apoptosis and DNA replication, *Mol. Cell. Biochem.,* 1999, 193:137–148.

Trucco et al., A dual approach in the study of poly (ADP–ribose) polymerase: in vitro random mutagenesis and generation of deficient mice, *Mol. Cell. Biochem.,* 1999, 193:53–60.

Weltin et al., Effect of 6(5H) –phenanthridinone, a poly (ADP–ribose)polymerase inhibitor, and ionizing radiation on the growth of cultured lymphoma cells, *Int. J. Radiat. Biol.,* 1997, 72:685–692.

\* cited by examiner

SEQUENCE LISTING

<160> NUMBER OF SEQ ID NOS: 345

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                               20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                               20

<210> SEQ ID NO 3
<211> LENGTH: 3660
<212> TYPE: DNA
<213> ORGANISM: Homo sapiens
<220> FEATURE:
<221> NAME/KEY: CDS
<222> LOCATION: (160)...(3204)

<400> SEQUENCE: 3
aatctatcag ggaacggcgg tggccggtgc ggcgtgttcg gtgcgctctg gccgctcagg      60
ccgtgcggct gggtgagcgc acgcgaggcg gcgaggcggc aagcgtgttt ctaggtcgtg     120
gcgtcgggct tccggagctt tggcggcagc taggggagg atg gcg gag tct tcg       174
                                            Met Ala Glu Ser Ser
                                              1               5 gat aag ctc tat cga gtc gag tac gcc aag agc ggg cgc gcc tct tgc      222
Asp Lys Leu Tyr Arg Val Glu Tyr Ala Lys Ser Gly Arg Ala Ser Cys
                10                  15                  20 aag aaa tgc agc gag agc atc ccc aag gac tcg ctc cgg atg gcc atc      270
Lys Lys Cys Ser Glu Ser Ile Pro Lys Asp Ser Leu Arg Met Ala Ile
            25                  30                  35 atg gtg cag tcg ccc atg ttt gat gga aaa gtc cca cac tgg tac cac      318
Met Val Gln Ser Pro Met Phe Asp Gly Lys Val Pro His Trp Tyr His
        40                  45                  50 ttc tcc tgc ttc tgg aag gtg ggc cac tcc atc cgg cac cct gac gtt      366
Phe Ser Cys Phe Trp Lys Val Gly His Ser Ile Arg His Pro Asp Val
    55                  60                  65 gag gtg gat ggg ttc tct gag ctt cgg tgg gat gac cag cag aaa gtc      414
Glu Val Asp Gly Phe Ser Glu Leu Arg Trp Asp Asp Gln Gln Lys Val
70                  75                  80                  85 aag aag aca gcg gaa gct gga gga gtg aca ggc aaa ggc cag gat gga      462
Lys Lys Thr Ala Glu Ala Gly Gly Val Thr Gly Lys Gly Gln Asp Gly
                90                  95                 100 att ggt agc aag gca gag aag act ctg ggt gac ttt gca gca gag tat      510
Ile Gly Ser Lys Ala Glu Lys Thr Leu Gly Asp Phe Ala Ala Glu Tyr
               105                 110                 115 gcc aag tcc aac aga agt acg tgc aag ggg tgt atg gag aag ata gaa      558
Ala Lys Ser Asn Arg Ser Thr Cys Lys Gly Cys Met Glu Lys Ile Glu
           120                 125                 130

-continued

| | |
|---|---|
| aag ggc cag gtg cgc ctg tcc aag aag atg gtg gac ccg gag aag cca<br>Lys Gly Gln Val Arg Leu Ser Lys Lys Met Val Asp Pro Glu Lys Pro<br>135              140                  145 | 606 |
| cag cta ggc atg att gac cgc tgg tac cat cca ggc tgc ttt gtc aag<br>Gln Leu Gly Met Ile Asp Arg Trp Tyr His Pro Gly Cys Phe Val Lys<br>150              155              160           165 | 654 |
| aac agg gag gag ctg ggt ttc cgg ccc gag tac agt gcg agt cag ctc<br>Asn Arg Glu Glu Leu Gly Phe Arg Pro Glu Tyr Ser Ala Ser Gln Leu<br>          170                175              180 | 702 |
| aag ggc ttc agc ctc ctt gct aca gag gat aaa gaa gcc ctg aag aag<br>Lys Gly Phe Ser Leu Leu Ala Thr Glu Asp Lys Glu Ala Leu Lys Lys<br>              185              190           195 | 750 |
| cag ctc cca gga gtc aag agt gaa gga aag aga aaa ggc gat gag gtg<br>Gln Leu Pro Gly Val Lys Ser Glu Gly Lys Arg Lys Gly Asp Glu Val<br>        200              205              210 | 798 |
| gat gga gtg gat gaa gtg gcg aag aag aaa tct aaa aaa gaa aaa gac<br>Asp Gly Val Asp Glu Val Ala Lys Lys Lys Ser Lys Lys Glu Lys Asp<br>215              220                  225 | 846 |
| aag gat agt aag ctt gaa aaa gcc cta aag gct cag aac gac ctg atc<br>Lys Asp Ser Lys Leu Glu Lys Ala Leu Lys Ala Gln Asn Asp Leu Ile<br>230              235              240           245 | 894 |
| tgg aac atc aag gac gag cta aag aaa gtg tgt tca act aat gac ctg<br>Trp Asn Ile Lys Asp Glu Leu Lys Lys Val Cys Ser Thr Asn Asp Leu<br>              250              255           260 | 942 |
| aag gag cta ctc atc ttc aac aag cag caa gtg cct tct ggg gag tcg<br>Lys Glu Leu Leu Ile Phe Asn Lys Gln Gln Val Pro Ser Gly Glu Ser<br>          265                270              275 | 990 |
| gcg atc ttg gac cga gta gct gat ggc atg gtg ttc ggt gcc ctc ctt<br>Ala Ile Leu Asp Arg Val Ala Asp Gly Met Val Phe Gly Ala Leu Leu<br>              280              285           290 | 1038 |
| ccc tgc gag gaa tgc tcg ggt cag ctg gtc ttc aag agc gat gcc tat<br>Pro Cys Glu Glu Cys Ser Gly Gln Leu Val Phe Lys Ser Asp Ala Tyr<br>295              300                  305 | 1086 |
| tac tgc act ggg gac gtc act gcc tgg acc aag tgt atg gtc aag aca<br>Tyr Cys Thr Gly Asp Val Thr Ala Trp Thr Lys Cys Met Val Lys Thr<br>310              315              320           325 | 1134 |
| cag aca ccc aac cgg aag gag tgg gta acc cca aag gaa ttc cga gaa<br>Gln Thr Pro Asn Arg Lys Glu Trp Val Thr Pro Lys Glu Phe Arg Glu<br>              330              335           340 | 1182 |
| atc tct tac ctc aag aaa ttg aag gtt aaa aag cag gac cgt ata ttc<br>Ile Ser Tyr Leu Lys Lys Leu Lys Val Lys Lys Gln Asp Arg Ile Phe<br>        345              350              355 | 1230 |
| ccc cca gaa acc agc gcc tcc gtg gcg gcc acg cct ccg ccc tcc aca<br>Pro Pro Glu Thr Ser Ala Ser Val Ala Ala Thr Pro Pro Pro Ser Thr<br>360              365                  370 | 1278 |
| gcc tcg gct cct gct gct gtg aac tcc tct gct tca gca gat aag cca<br>Ala Ser Ala Pro Ala Ala Val Asn Ser Ser Ala Ser Ala Asp Lys Pro<br>375              380              385 | 1326 |
| tta tcc aac atg aag atc ctg act ctc ggg aag ctg tcc cgg aac aag<br>Leu Ser Asn Met Lys Ile Leu Thr Leu Gly Lys Leu Ser Arg Asn Lys<br>390              395              400           405 | 1374 |
| gat gaa gtg aag gcc atg att gag aaa ctc ggg ggg aag ttg acg ggg<br>Asp Glu Val Lys Ala Met Ile Glu Lys Leu Gly Gly Lys Leu Thr Gly<br>              410              415           420 | 1422 |
| acg gcc aac aag gct tcc ctg tgc atc agc acc aaa aag gag gtg gaa<br>Thr Ala Asn Lys Ala Ser Leu Cys Ile Ser Thr Lys Lys Glu Val Glu<br>          425              430              435 | 1470 |
| aag atg aat aag aag atg gag gaa gta aag gaa gcc aac atc cga gtt<br>Lys Met Asn Lys Lys Met Glu Glu Val Lys Glu Ala Asn Ile Arg Val<br>              440              445           450 | 1518 |

```
gtg tct gag gac ttc ctc cag gac gtc tcc gcc tcc acc aag agc ctt    1566
Val Ser Glu Asp Phe Leu Gln Asp Val Ser Ala Ser Thr Lys Ser Leu
    455                 460                 465 cag gag ttg ttc tta gcg cac atc ttg tcc cct tgg ggg gca gag gtg    1614
Gln Glu Leu Phe Leu Ala His Ile Leu Ser Pro Trp Gly Ala Glu Val
470                 475                 480                 485 aag gca gag cct gtt gaa gtt gtg gcc cca aga ggg aag tca ggg gct    1662
Lys Ala Glu Pro Val Glu Val Val Ala Pro Arg Gly Lys Ser Gly Ala
                490                 495                 500 gcg ctc tcc aaa aaa agc aag ggc cag gtc aag gag gaa ggt atc aac    1710
Ala Leu Ser Lys Lys Ser Lys Gly Gln Val Lys Glu Glu Gly Ile Asn
            505                 510                 515 aaa tct gaa aag aga atg aaa tta act ctt aaa gga gga gca gct gtg    1758
Lys Ser Glu Lys Arg Met Lys Leu Thr Leu Lys Gly Gly Ala Ala Val
        520                 525                 530 gat cct gat tct gga ctg gaa cac tct gcg cat gtc ctg gag aaa ggt    1806
Asp Pro Asp Ser Gly Leu Glu His Ser Ala His Val Leu Glu Lys Gly
    535                 540                 545 ggg aag gtc ttc agt gcc acc ctt ggc ctg gtg gac atc gtt aaa gga    1854
Gly Lys Val Phe Ser Ala Thr Leu Gly Leu Val Asp Ile Val Lys Gly
550                 555                 560                 565 acc aac tcc tac tac aag ctg cag ctt ctg gag gac gac aag gaa aac    1902
Thr Asn Ser Tyr Tyr Lys Leu Gln Leu Leu Glu Asp Asp Lys Glu Asn
                570                 575                 580 agg tat tgg ata ttc agg tcc tgg ggc cgt gtg ggt acg gtg atc ggt    1950
Arg Tyr Trp Ile Phe Arg Ser Trp Gly Arg Val Gly Thr Val Ile Gly
            585                 590                 595 agc aac aaa ctg gaa cag atg ccg tcc aag gag gat gcc att gag cag    1998
Ser Asn Lys Leu Glu Gln Met Pro Ser Lys Glu Asp Ala Ile Glu Gln
        600                 605                 610 ttc atg aaa tta tat gaa gaa aaa acc ggg aac gct tgg cac tcc aaa    2046
Phe Met Lys Leu Tyr Glu Glu Lys Thr Gly Asn Ala Trp His Ser Lys
    615                 620                 625 aat ttc acg aag tat ccc aaa aag ttt tac ccc ctg gag att gac tat    2094
Asn Phe Thr Lys Tyr Pro Lys Lys Phe Tyr Pro Leu Glu Ile Asp Tyr
630                 635                 640                 645 ggc cag gat gaa gag gca gtg aag aag ctc aca gta aat cct ggc acc    2142
Gly Gln Asp Glu Glu Ala Val Lys Lys Leu Thr Val Asn Pro Gly Thr
                650                 655                 660 aag tcc aag ctc ccc aag cca gtt cag gac ctc atc aag atg atc ttt    2190
Lys Ser Lys Leu Pro Lys Pro Val Gln Asp Leu Ile Lys Met Ile Phe
            665                 670                 675 gat gtg gaa agt atg aag aaa gcc atg gtg gag tat gag atc gac ctt    2238
Asp Val Glu Ser Met Lys Lys Ala Met Val Glu Tyr Glu Ile Asp Leu
        680                 685                 690 cag aag atg ccc ttg ggg aag ctg agc aaa agg cag atc cag gcc gca    2286
Gln Lys Met Pro Leu Gly Lys Leu Ser Lys Arg Gln Ile Gln Ala Ala
    695                 700                 705 tac tcc atc ctc agt gag gtc cag cag gcg gtg tct cag ggc agc agc    2334
Tyr Ser Ile Leu Ser Glu Val Gln Gln Ala Val Ser Gln Gly Ser Ser
710                 715                 720                 725 gac tct cag atc ctg gat ctc tca aat cgc ttt tac acc ctg atc ccc    2382
Asp Ser Gln Ile Leu Asp Leu Ser Asn Arg Phe Tyr Thr Leu Ile Pro
                730                 735                 740 cac gac ttt ggg atg aag aag cct ccg ctc ctg aac aat gca gac agt    2430
His Asp Phe Gly Met Lys Lys Pro Pro Leu Leu Asn Asn Ala Asp Ser
            745                 750                 755 gtg cag gcc aag gtg gaa atg ctt gac aac ctg ctg gac atc gag gtg    2478
Val Gln Ala Lys Val Glu Met Leu Asp Asn Leu Leu Asp Ile Glu Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 760 |     |     |     |     | 765 |     |     |     |     | 770 |     |     |     |      |
| gcc | tac | agt | ctg | ctc | agg | gga | ggg | tct | gat | gat | agc | agc | aag | gat | ccc | 2526 |
| Ala | Tyr | Ser | Leu | Leu | Arg | Gly | Gly | Ser | Asp | Asp | Ser | Ser | Lys | Asp | Pro |      |
|     |     | 775 |     |     |     |     | 780 |     |     |     |     | 785 |     |     |     |      |
| atc | gat | gtc | aac | tat | gag | aag | ctc | aaa | act | gac | att | aag | gtg | gtt | gac | 2574 |
| Ile | Asp | Val | Asn | Tyr | Glu | Lys | Leu | Lys | Thr | Asp | Ile | Lys | Val | Val | Asp |      |
| 790 |     |     |     |     | 795 |     |     |     |     | 800 |     |     |     |     | 805 |      |
| aga | gat | tct | gaa | gaa | gcc | gag | atc | atc | agg | aag | tat | gtt | aag | aac | act | 2622 |
| Arg | Asp | Ser | Glu | Glu | Ala | Glu | Ile | Ile | Arg | Lys | Tyr | Val | Lys | Asn | Thr |      |
|     |     |     |     | 810 |     |     |     |     | 815 |     |     |     |     | 820 |     |      |
| cat | gca | acc | aca | cac | agt | gcg | tat | gac | ttg | gaa | gtc | atc | gat | atc | ttt | 2670 |
| His | Ala | Thr | Thr | His | Ser | Ala | Tyr | Asp | Leu | Glu | Val | Ile | Asp | Ile | Phe |      |
|     |     |     |     | 825 |     |     |     |     | 830 |     |     |     |     | 835 |     |      |
| aag | ata | gag | cgt | gaa | ggc | gaa | tgc | cag | cgt | tac | aag | ccc | ttt | aag | cag | 2718 |
| Lys | Ile | Glu | Arg | Glu | Gly | Glu | Cys | Gln | Arg | Tyr | Lys | Pro | Phe | Lys | Gln |      |
|     |     |     | 840 |     |     |     |     | 845 |     |     |     |     | 850 |     |     |      |
| ctt | cat | aac | cga | aga | ttg | ctg | tgg | cac | ggg | tcc | agg | acc | acc | aac | ttt | 2766 |
| Leu | His | Asn | Arg | Arg | Leu | Leu | Trp | His | Gly | Ser | Arg | Thr | Thr | Asn | Phe |      |
|     |     | 855 |     |     |     |     | 860 |     |     |     |     | 865 |     |     |     |      |
| gct | ggg | atc | ctg | tcc | cag | ggt | ctt | cgg | ata | gcc | ccg | cct | gaa | gcg | ccc | 2814 |
| Ala | Gly | Ile | Leu | Ser | Gln | Gly | Leu | Arg | Ile | Ala | Pro | Pro | Glu | Ala | Pro |      |
| 870 |     |     |     |     | 875 |     |     |     |     | 880 |     |     |     |     | 885 |      |
| gtg | aca | ggc | tac | atg | ttt | ggt | aaa | ggg | atc | tat | ttc | gct | gac | atg | gtc | 2862 |
| Val | Thr | Gly | Tyr | Met | Phe | Gly | Lys | Gly | Ile | Tyr | Phe | Ala | Asp | Met | Val |      |
|     |     |     |     | 890 |     |     |     |     | 895 |     |     |     |     | 900 |     |      |
| tcc | aag | agt | gcc | aac | tac | tac | cat | acg | tct | cag | gga | gac | cca | ata | ggc | 2910 |
| Ser | Lys | Ser | Ala | Asn | Tyr | Tyr | His | Thr | Ser | Gln | Gly | Asp | Pro | Ile | Gly |      |
|     |     |     |     | 905 |     |     |     |     | 910 |     |     |     |     | 915 |     |      |
| tta | atc | ctg | ttg | gga | gaa | gtt | gcc | ctt | gga | aac | atg | tat | gaa | ctg | aag | 2958 |
| Leu | Ile | Leu | Leu | Gly | Glu | Val | Ala | Leu | Gly | Asn | Met | Tyr | Glu | Leu | Lys |      |
|     |     |     | 920 |     |     |     |     | 925 |     |     |     |     | 930 |     |     |      |
| cac | gct | tca | cat | atc | agc | agg | tta | ccc | aag | ggc | aag | cac | agt | gtc | aaa | 3006 |
| His | Ala | Ser | His | Ile | Ser | Arg | Leu | Pro | Lys | Gly | Lys | His | Ser | Val | Lys |      |
|     |     | 935 |     |     |     |     | 940 |     |     |     |     | 945 |     |     |     |      |
| ggt | ttg | ggc | aaa | act | acc | cct | gat | cct | tca | gct | aac | att | agt | ctg | gat | 3054 |
| Gly | Leu | Gly | Lys | Thr | Thr | Pro | Asp | Pro | Ser | Ala | Asn | Ile | Ser | Leu | Asp |      |
| 950 |     |     |     |     | 955 |     |     |     |     | 960 |     |     |     |     | 965 |      |
| ggt | gta | gac | gtt | cct | ctt | ggg | acc | ggg | att | tca | tct | ggt | gtg | ata | gac | 3102 |
| Gly | Val | Asp | Val | Pro | Leu | Gly | Thr | Gly | Ile | Ser | Ser | Gly | Val | Ile | Asp |      |
|     |     |     |     | 970 |     |     |     |     | 975 |     |     |     |     | 980 |     |      |
| acc | tct | cta | cta | tat | aac | gag | tac | att | gtc | tat | gat | att | gct | cag | gta | 3150 |
| Thr | Ser | Leu | Leu | Tyr | Asn | Glu | Tyr | Ile | Val | Tyr | Asp | Ile | Ala | Gln | Val |      |
|     |     |     | 985 |     |     |     |     | 990 |     |     |     |     | 995 |     |     |      |
| aat | ctg | aag | tat | ctg | ctg | aaa | ctg | aaa | ttc | aat | ttt | aag | acc | tcc | ctg | 3198 |
| Asn | Leu | Lys | Tyr | Leu | Leu | Lys | Leu | Lys | Phe | Asn | Phe | Lys | Thr | Ser | Leu |      |
|     |     |     | 1000|     |     |     |     | 1005|     |     |     |     | 1010|     |     |      |

| | |
|---|---|
| tgg taa ttgggagagg tagccgagtc acaccggtg gctgtggtat gaattcaccc<br>Trp | 3254 |
| gaagcgcttc tgcaccaact cacctggccg ctaagttgct gatgggtagt acctgtacta | 3314 |
| aaccacctca gaaaggattt tacagaaacg tgttaaaggt tttctctaac ttctcaagtc | 3374 |
| ccttgttttg tgttgtgtct gtggggaggg gttgttttgg ggttgttttt gttttttctt | 3434 |
| gccaggtaga taaaactgac atagagaaaa ggctggagag agattctgtt gcatagacta | 3494 |
| gtcctatgga aaaaccaaa gcttcgttag aatgtctgcc ttactggttt ccccagggaa | 3554 |
| ggaaaaatac acttccaccc tttttctaa gtgttcgtct ttagttttga ttttggaaag | 3614 |
| atgttaagca tttattttta gttaaaataa aaactaattt catact | 3660 |

```
<210> SEQ ID NO 4
<211> LENGTH: 19
<212> TYPE: DNA
<213> ORGANISM: Artificial Sequence
<220> FEATURE:
<223> OTHER INFORMATION: PCR Primer

<400> SEQUENCE: 4
cctgatcccc cacgacttt                                                  19

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
caccttggcc tgcacactg                                                  19

<210> SEQ ID NO 6
<211> LENGTH: 24
<212> TYPE: DNA
<213> ORGANISM: Artificial Sequence
<220> FEATURE:
<223> OTHER INFORMATION: PCR Probe

<400> SEQUENCE: 6
aagcctccgc tcctgaacaa tgca                                            24

<210> SEQ ID NO 7
<211> LENGTH: 1910
<212> TYPE: DNA
<213> ORGANISM: Homo sapiens
<220> FEATURE:
<221> NAME/KEY: CDS
<222> LOCATION: (173)...(1777)

<400> SEQUENCE: 7
ctagaattca gcggccgctg aattctaggc ggcgcggcgg cgacggagca ccggcggcgg      60
cagggcgaga gcattaaatg aaagcaaaag agttaataat ggcaacacgg ctccagaaga     120
ctcttcccct gccaagaaaa ctcgtagatg ccagagacag gagtcgaaaa ag atg cct    178
                                                          Met Pro
                                                            1 gtg gct gga gga aaa gct aat aag gac agg aca gaa gac aag caa gat     226
Val Ala Gly Gly Lys Ala Asn Lys Asp Arg Thr Glu Asp Lys Gln Asp
         5                  10                  15 ggt atg cca gga agg tca tgg gcc agc aaa agg gtc tct gaa tct gtg     274
Gly Met Pro Gly Arg Ser Trp Ala Ser Lys Arg Val Ser Glu Ser Val
     20                  25                  30 aag gcc ttg ctg tta aag ggc aaa gct cct gtg gac cca gag tgt aca     322
Lys Ala Leu Leu Leu Lys Gly Lys Ala Pro Val Asp Pro Glu Cys Thr
 35                  40                  45                  50 gcc aag gtg ggg aag gct cat gtg tat tgt gaa gga aat gat gtc tat     370
Ala Lys Val Gly Lys Ala His Val Tyr Cys Glu Gly Asn Asp Val Tyr
                 55                  60                  65 gat gtc atg cta aat cag acc aat ctc cag ttc aac aac aac aag tac     418
Asp Val Met Leu Asn Gln Thr Asn Leu Gln Phe Asn Asn Asn Lys Tyr
             70                  75                  80 tat ctg att cag cta tta gaa gat gat gcc cag agg aac ttc agt gtt     466
Tyr Leu Ile Gln Leu Leu Glu Asp Asp Ala Gln Arg Asn Phe Ser Val
         85                  90                  95
```

```
tgg atg aga tgg ggc cga gtt ggg aaa atg gga cag cac agc ctg gtg       514
Trp Met Arg Trp Gly Arg Val Gly Lys Met Gly Gln His Ser Leu Val
    100                 105                 110 gct tgt tca ggc aat ctc aac aag gcc aag gaa atc ttt cag aag aaa       562
Ala Cys Ser Gly Asn Leu Asn Lys Ala Lys Glu Ile Phe Gln Lys Lys
115                 120                 125                 130 ttc ctt gac aaa acg aaa aac aat tgg gaa gat cga gaa aag ttt gag       610
Phe Leu Asp Lys Thr Lys Asn Asn Trp Glu Asp Arg Glu Lys Phe Glu
                135                 140                 145 aag gtg cct gga aaa tat gat atg cta cag atg gac tat gcc acc aat       658
Lys Val Pro Gly Lys Tyr Asp Met Leu Gln Met Asp Tyr Ala Thr Asn
            150                 155                 160 act cag gat gaa gag gaa aca aaa aaa gag gaa tct ctt aaa tct ccc       706
Thr Gln Asp Glu Glu Glu Thr Lys Lys Glu Glu Ser Leu Lys Ser Pro
        165                 170                 175 ttg aag cca gag tca cag cta gat ctt cgg gta cag gag tta ata aag       754
Leu Lys Pro Glu Ser Gln Leu Asp Leu Arg Val Gln Glu Leu Ile Lys
    180                 185                 190 ttg atc tgt aat gtt cag gcc atg gaa gaa atg atg atg gaa atg aag       802
Leu Ile Cys Asn Val Gln Ala Met Glu Glu Met Met Met Glu Met Lys
195                 200                 205                 210 tat aat acc aag aaa gcc cca ctt ggg aag ctg aca gtg gca caa atc       850
Tyr Asn Thr Lys Lys Ala Pro Leu Gly Lys Leu Thr Val Ala Gln Ile
                215                 220                 225 aag gca ggt tac cag tct ctt aag aag att gag gat tgt att cgg gct       898
Lys Ala Gly Tyr Gln Ser Leu Lys Lys Ile Glu Asp Cys Ile Arg Ala
            230                 235                 240 ggc cag cat gga cga gct ctc atg gaa gca tgc aat gaa ttc tac acc       946
Gly Gln His Gly Arg Ala Leu Met Glu Ala Cys Asn Glu Phe Tyr Thr
        245                 250                 255 agg att ccg cat gac ttt gga ctc cgt act cct cca cta atc cgg aca       994
Arg Ile Pro His Asp Phe Gly Leu Arg Thr Pro Pro Leu Ile Arg Thr
    260                 265                 270 cag aag gaa ctg tca gaa aaa ata caa tta cta gag gct ttg gga gac      1042
Gln Lys Glu Leu Ser Glu Lys Ile Gln Leu Leu Glu Ala Leu Gly Asp
275                 280                 285                 290 att gaa att gct att aag ctg gtg aaa aca gag cta caa agc cca gaa      1090
Ile Glu Ile Ala Ile Lys Leu Val Lys Thr Glu Leu Gln Ser Pro Glu
                295                 300                 305 cac cca ttg gac caa cac tat aga aac cta cat tgt gcc ttg cgc ccc      1138
His Pro Leu Asp Gln His Tyr Arg Asn Leu His Cys Ala Leu Arg Pro
            310                 315                 320 ctt gac cat gaa agt tac gag ttc aaa gtg att tcc cag tac cta caa      1186
Leu Asp His Glu Ser Tyr Glu Phe Lys Val Ile Ser Gln Tyr Leu Gln
        325                 330                 335 tct acc cat gct ccc aca cac agc gac tat acc atg acc ttg ctg gat      1234
Ser Thr His Ala Pro Thr His Ser Asp Tyr Thr Met Thr Leu Leu Asp
    340                 345                 350 ttg ttt gaa gtg gag aag gat ggt gag aaa gaa gcc ttc aga gag gac      1282
Leu Phe Glu Val Glu Lys Asp Gly Glu Lys Glu Ala Phe Arg Glu Asp
355                 360                 365                 370 ctt cat aac agg atg ctt cta tgg cat ggt tcc agg atg agt aac tgg      1330
Leu His Asn Arg Met Leu Leu Trp His Gly Ser Arg Met Ser Asn Trp
                375                 380                 385 gtg gga atc ttg agc cat ggg ctt cga att gcc cac cct gaa gct ccc      1378
Val Gly Ile Leu Ser His Gly Leu Arg Ile Ala His Pro Glu Ala Pro
            390                 395                 400 atc aca ggt tac atg ttt ggg aaa gga atc tac ttt gct gac atg tct      1426
Ile Thr Gly Tyr Met Phe Gly Lys Gly Ile Tyr Phe Ala Asp Met Ser
        405                 410                 415
```

```
tcc aag agt gcc aat tac tgc ttt gcc tct cgc cta aag aat aca gga      1474
Ser Lys Ser Ala Asn Tyr Cys Phe Ala Ser Arg Leu Lys Asn Thr Gly
    420                 425                 430 ctg ctg ctc tta tca gag gta gct cta ggt cag tgt aat gaa cta cta      1522
Leu Leu Leu Leu Ser Glu Val Ala Leu Gly Gln Cys Asn Glu Leu Leu
435                 440                 445                 450 gag gcc aat cct aag gcc gaa gga ttg ctt caa ggt aaa cat agc acc      1570
Glu Ala Asn Pro Lys Ala Glu Gly Leu Leu Gln Gly Lys His Ser Thr
                455                 460                 465 aag ggg ctg ggc aag atg gct ccc agt tct gcc cac ttc gtc acc ctg      1618
Lys Gly Leu Gly Lys Met Ala Pro Ser Ser Ala His Phe Val Thr Leu
            470                 475                 480 aat ggg agt aca gtg cca tta gga cca gca agt gac aca gga att ctg      1666
Asn Gly Ser Thr Val Pro Leu Gly Pro Ala Ser Asp Thr Gly Ile Leu
        485                 490                 495 aat cca gat ggt tat acc ctc aac tac aat gaa tat att gta tat aac      1714
Asn Pro Asp Gly Tyr Thr Leu Asn Tyr Asn Glu Tyr Ile Val Tyr Asn
    500                 505                 510 ccc aac cag gtc cgt atg cgg tac ctt tta aag gtt cag ttt aat ttc      1762
Pro Asn Gln Val Arg Met Arg Tyr Leu Leu Lys Val Gln Phe Asn Phe
515                 520                 525                 530 ctt cag ctg tgg tga atgttgatct taaataaacc agagatctga tcttcaagca      1817
Leu Gln Leu Trp agaaaataag cagtgttgta cttgtgaatt ttgtgatatt ttatgtaata aaaactgtac    1877
aggtctaaaa aaaaaaaaaa aaaaaaaaaa aaa                                 1910

<210> SEQ ID NO 8
<211> LENGTH: 21
<212> TYPE: DNA
<213> ORGANISM: Artificial Sequence
<220> FEATURE:
<223> OTHER INFORMATION: PCR Primer

<400> SEQUENCE: 8
agaagactct tcccctgcca a                                              21

<210> SEQ ID NO 9
<211> LENGTH: 19
<212> TYPE: DNA
<213> ORGANISM: Artificial Sequence
<220> FEATURE:
<223> OTHER INFORMATION: PCR Primer

<400> SEQUENCE: 9
cctccagcca caggcatct                                                 19

<210> SEQ ID NO 10
<211> LENGTH: 30
<212> TYPE: DNA
<213> ORGANISM: Artificial Sequence
<220> FEATURE:
<223> OTHER INFORMATION: PCR Probe

<400> SEQUENCE: 10
aaactcgtag atgccagaga caggagtcga                                     30

<210> SEQ ID NO 11
<211> LENGTH: 1880
<212> TYPE: DNA
<213> ORGANISM: Homo sapiens
<220> FEATURE:
<221> NAME/KEY: CDS
```

<222> LOCATION: (131)...(1732)

<400> SEQUENCE: 11

| | | |
|---|---|---|
| attctctccc taattcacgc ctgaggctca tggagagttg ctagacctgg gactgccctg | | 60 |
| ggaggcgcac acaaccaggc cgggtggcag ccaggacctc tcccatgtcc ctgcttttct | | 120 |
| tgggacagcc atg gct cca aag ccg aag ccc tgg gta cag act gag ggc<br>              Met Ala Pro Lys Pro Lys Pro Trp Val Gln Thr Glu Gly<br>               1               5                    10 | | 169 |
| cct gag aag aag aag ggc cgg cag gca gga agg gag gag gac ccc ttc<br>Pro Glu Lys Lys Lys Gly Arg Gln Ala Gly Arg Glu Glu Asp Pro Phe<br> 15                       20                    25 | | 217 |
| cgc tcc acc gct gag gcc ctc aag gcc ata ccc gca gag aag cgc ata<br>Arg Ser Thr Ala Glu Ala Leu Lys Ala Ile Pro Ala Glu Lys Arg Ile<br> 30                       35                    40                   45 | | 265 |
| atc cgc gtg gat cca aca tgt cca ctc agc agc aac ccc ggg acc cag<br>Ile Arg Val Asp Pro Thr Cys Pro Leu Ser Ser Asn Pro Gly Thr Gln<br>                    50                    55                    60 | | 313 |
| gtg tat gag gac tac aac tgc acc ctg aac cag acc aac atc gag aac<br>Val Tyr Glu Asp Tyr Asn Cys Thr Leu Asn Gln Thr Asn Ile Glu Asn<br>             65                    70                    75 | | 361 |
| aac aac aag aag ttc tac atc atc cag ctg ctc caa gac agc aac cgc<br>Asn Asn Lys Lys Phe Tyr Ile Ile Gln Leu Leu Gln Asp Ser Asn Arg<br>      80                    85                    90 | | 409 |
| ttc ttc acc tgc tgg aac cgc tgg ggc cgt gtg gga gag gtc ggc cag<br>Phe Phe Thr Cys Trp Asn Arg Trp Gly Arg Val Gly Glu Val Gly Gln<br>     95                   100                105 | | 457 |
| tca aag atc aac cac ttc aca agg cta gaa gat gca aag aag gac ttt<br>Ser Lys Ile Asn His Phe Thr Arg Leu Glu Asp Ala Lys Lys Asp Phe<br>110                     115                   120               125 | | 505 |
| gag aag aaa ttt cgg gaa aag acc aag aac aac tgg gca gag cgg gac<br>Glu Lys Lys Phe Arg Glu Lys Thr Lys Asn Asn Trp Ala Glu Arg Asp<br>                    130                    135                  140 | | 553 |
| cac ttt gtg tct cac ccg ggc aag tac aca ctt atc gaa gta cag gca<br>His Phe Val Ser His Pro Gly Lys Tyr Thr Leu Ile Glu Val Gln Ala<br>                   145                    150               155 | | 601 |
| gag gat gag gcc cag gaa gct gtg gtg aag gtg gac aga gcc cca gtg<br>Glu Asp Glu Ala Gln Glu Ala Val Val Lys Val Asp Arg Ala Pro Val<br>             160                    165                170 | | 649 |
| agg act gtg act aag cgg gtg cag ccc tgc tcc ctg gac cca gcc acg<br>Arg Thr Val Thr Lys Arg Val Gln Pro Cys Ser Leu Asp Pro Ala Thr<br>175                     180                   185 | | 697 |
| cag aag ctc atc act aac atc ttc agc aag gag atg ttc aag aac acc<br>Gln Lys Leu Ile Thr Asn Ile Phe Ser Lys Glu Met Phe Lys Asn Thr<br>190                     195                   200               205 | | 745 |
| atg gcc ctc atg gac ctg gat gtg aag aag atg ccc ctg gga aag ctg<br>Met Ala Leu Met Asp Leu Asp Val Lys Lys Met Pro Leu Gly Lys Leu<br>                    210                    215                  220 | | 793 |
| agc aag caa cag att gca cgg ggt ttc gag gcc ttg gag gcg ctg gag<br>Ser Lys Gln Gln Ile Ala Arg Gly Phe Glu Ala Leu Glu Ala Leu Glu<br>                 225                    230               235 | | 841 |
| gag gcc ctg aaa ggc ccc acg gat ggt ggc caa agc ctg gag gag ctg<br>Glu Ala Leu Lys Gly Pro Thr Asp Gly Gly Gln Ser Leu Glu Glu Leu<br>             240                    245                250 | | 889 |
| tcc tca cac ttt tac acc gtc atc ccg cac aac ttc ggc cac agc cag<br>Ser Ser His Phe Tyr Thr Val Ile Pro His Asn Phe Gly His Ser Gln<br>255                     260                   265 | | 937 |
| ccc ccg ccc atc aat tcc cct gag ctt ctg cag gcc aag aag gac atg<br>Pro Pro Pro Ile Asn Ser Pro Glu Leu Leu Gln Ala Lys Lys Asp Met<br>270                     275                   280               285 | | 985 |

-continued

```
ctg ctg gtg ctg gcg gac atc gag ctg gcc cag gcc ctg cag gca gtc      1033
Leu Leu Val Leu Ala Asp Ile Glu Leu Ala Gln Ala Leu Gln Ala Val
                    290                 295                 300 tct gag cag gag aag acg gtg gag gag gtg cca cac ccc ctg gac cga      1081
Ser Glu Gln Glu Lys Thr Val Glu Glu Val Pro His Pro Leu Asp Arg
            305                 310                 315 gac tac cag ctt ctc aag tgc cag ctg cag ctg cta gac tct gga gca      1129
Asp Tyr Gln Leu Leu Lys Cys Gln Leu Gln Leu Leu Asp Ser Gly Ala
        320                 325                 330 cct gag tac aag gtg ata cag acc tac tta gaa cag act ggc agc aac      1177
Pro Glu Tyr Lys Val Ile Gln Thr Tyr Leu Glu Gln Thr Gly Ser Asn
    335                 340                 345 cac agg tgc cct aca ctt caa cac atc tgg aaa gta aac caa gaa ggg      1225
His Arg Cys Pro Thr Leu Gln His Ile Trp Lys Val Asn Gln Glu Gly
350                 355                 360                 365 gag gaa gac aga ttc cag gcc cac tcc aaa ctg ggt aat cgg aag ctg      1273
Glu Glu Asp Arg Phe Gln Ala His Ser Lys Leu Gly Asn Arg Lys Leu
                370                 375                 380 ctg tgg cat ggc acc aac atg gcc gtg gtg gcc gcc atc ctc act agt      1321
Leu Trp His Gly Thr Asn Met Ala Val Val Ala Ala Ile Leu Thr Ser
            385                 390                 395 ggg ctc cgc atc atg cca cat tct ggt ggg cgt gtt ggc aag ggc atc      1369
Gly Leu Arg Ile Met Pro His Ser Gly Gly Arg Val Gly Lys Gly Ile
        400                 405                 410 tac ttt gcc tca gag aac agc aag tca gct gga tat gtt att ggc atg      1417
Tyr Phe Ala Ser Glu Asn Ser Lys Ser Ala Gly Tyr Val Ile Gly Met
    415                 420                 425 aag tgt ggg gcc cac cat gtc ggc tac atg ttc ctg ggt gag gtg gcc      1465
Lys Cys Gly Ala His His Val Gly Tyr Met Phe Leu Gly Glu Val Ala
430                 435                 440                 445 ctg ggc aga gag cac cat atc aac acg gac aac ccc agc ttg aag agc      1513
Leu Gly Arg Glu His His Ile Asn Thr Asp Asn Pro Ser Leu Lys Ser
                450                 455                 460 cca cct cct ggc ttc gac agt gtc att gcc cga ggc cac acc gag cct      1561
Pro Pro Pro Gly Phe Asp Ser Val Ile Ala Arg Gly His Thr Glu Pro
            465                 470                 475 gat ccg acc cag gac act gag ttg gag ctg gat ggc cag caa gtg gtg      1609
Asp Pro Thr Gln Asp Thr Glu Leu Glu Leu Asp Gly Gln Gln Val Val
        480                 485                 490 gtg ccc cag ggc cag cct gtg ccc tgc cca gag ttc agc agc tcc aca      1657
Val Pro Gln Gly Gln Pro Val Pro Cys Pro Glu Phe Ser Ser Ser Thr
    495                 500                 505 ttc tcc cag agc gag tac ctc atc tac cag gag agc cag tgt cgc ctg      1705
Phe Ser Gln Ser Glu Tyr Leu Ile Tyr Gln Glu Ser Gln Cys Arg Leu
510                 515                 520                 525 cgc tac ctg ctg gag gtc cac ctc tga gtgcccgccc tgtccccgg             1752
Arg Tyr Leu Leu Glu Val His Leu
                530 ggtcctgcaa ggctggactg tgatcttcaa tcatcctgcc catctctggt accctatat    1812 cactcctttt tttcaagaat acaatacgtt gttgttaact ataaaaaaaa aaaaaaaaaa   1872 aaaaaaaa                                                            1880

<210> SEQ ID NO 12
<211> LENGTH: 21
<212> TYPE: DNA
<213> ORGANISM: Artificial Sequence
<220> FEATURE:
<223> OTHER INFORMATION: PCR Primer
```

-continued

```
<400> SEQUENCE: 12
cctcatggac ctggatgtga a                                              21

<210> SEQ ID NO 13
<211> LENGTH: 20
<212> TYPE: DNA
<213> ORGANISM: Artificial Sequence
<220> FEATURE:
<223> OTHER INFORMATION: PCR Primer

<400> SEQUENCE: 13 gaaacccgt gcaatctgtt                                                 20

<210> SEQ ID NO 14
<211> LENGTH: 24
<212> TYPE: DNA
<213> ORGANISM: Artificial Sequence
<220> FEATURE:
<223> OTHER INFORMATION: PCR Probe

<400> SEQUENCE: 14
atgcccctgg gaaagctgag caag                                           24

<210> SEQ ID NO 15
<211> LENGTH: 19
<212> TYPE: DNA
<213> ORGANISM: Artificial Sequence
<220> FEATURE:
<223> OTHER INFORMATION: PCR Primer

<400> SEQUENCE: 15
gaaggtgaag gtcggagtc                                                 19

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gaagatggtg atgggatttc                                                20

<210> SEQ ID NO 17
<211> LENGTH: 20
<212> TYPE: DNA
<213> ORGANISM: Artificial Sequence
<220> FEATURE:
<223> OTHER INFORMATION: PCR Probe

<400> SEQUENCE: 17
caagcttccc gttctcagcc                                                20

<210> SEQ ID NO 18
<211> LENGTH: 1766
<212> TYPE: DNA
<213> ORGANISM: Mus musculus
<220> FEATURE:
<221> NAME/KEY: CDS
<222> LOCATION: (89)...(1657)

<400> SEQUENCE: 18
aggctctgga aggcgagtgc taaatgaagc caagaaagtt gataatggca acaaagcaac    60
agaagacgac tctcctcctg gcaagaag atg cgc acg tgc cag aga aaa ggg      112
                              Met Arg Thr Cys Gln Arg Lys Gly
```

```
                          1                 5
cct atg gct gga ggg aag gac gca gac agg aca aaa gac aat cga gac    160
Pro Met Ala Gly Gly Lys Asp Ala Asp Arg Thr Lys Asp Asn Arg Asp
     10              15                  20 tct gtg aag acc ttg ctg tta aag ggc aaa gcc cct gtg gac cca gag    208
Ser Val Lys Thr Leu Leu Leu Lys Gly Lys Ala Pro Val Asp Pro Glu
 25              30                  35                  40 tgt gca gcc aag ctg gga aag gct cat gtg tat tgt gaa gga gat gat    256
Cys Ala Ala Lys Leu Gly Lys Ala His Val Tyr Cys Glu Gly Asp Asp
                 45                  50                  55 gtc tat gat gtc atg cta aat caa acc aat ctc cag ttc aac aac aac    304
Val Tyr Asp Val Met Leu Asn Gln Thr Asn Leu Gln Phe Asn Asn Asn
                 60                  65                  70 aag tac tac ctt att cag ctg tta gaa gat gat gcc cag agg aac ttc    352
Lys Tyr Tyr Leu Ile Gln Leu Leu Glu Asp Asp Ala Gln Arg Asn Phe
             75                  80                  85 agt gtt tgg atg agg tgg ggc cga gtt gga aag acg ggg cag cac agc    400
Ser Val Trp Met Arg Trp Gly Arg Val Gly Lys Thr Gly Gln His Ser
 90                  95                 100 ttg gtg act tgt tct ggt gac ctc aac aaa gca aaa gaa ata ttt cag    448
Leu Val Thr Cys Ser Gly Asp Leu Asn Lys Ala Lys Glu Ile Phe Gln
105                 110                 115                 120 aaa aaa ttc ctt gac aaa act aaa aac aat tgg gag gac cgt gag aac    496
Lys Lys Phe Leu Asp Lys Thr Lys Asn Asn Trp Glu Asp Arg Glu Asn
                125                 130                 135 ttt gaa aaa gta cct gga aaa tac gac atg tta cag atg gac tat gct    544
Phe Glu Lys Val Pro Gly Lys Tyr Asp Met Leu Gln Met Asp Tyr Ala
                140                 145                 150 gcc agc acg cag gat gaa agt aaa aca aaa gaa gag gaa act ttg aag    592
Ala Ser Thr Gln Asp Glu Ser Lys Thr Lys Glu Glu Glu Thr Leu Lys
        155                 160                 165 cct gag tct cag ctg gat ctt cga gtc cag gag ctg cta aag ttg atc    640
Pro Glu Ser Gln Leu Asp Leu Arg Val Gln Glu Leu Leu Lys Leu Ile
170                 175                 180 tgt aac gtg cag acc atg gaa gaa atg atg att gag atg aag tat gac    688
Cys Asn Val Gln Thr Met Glu Glu Met Met Ile Glu Met Lys Tyr Asp
185                 190                 195                 200 acc aag aga gcc ccg ctt gga aag ctg aca gtg gcg caa atc aag gcc    736
Thr Lys Arg Ala Pro Leu Gly Lys Leu Thr Val Ala Gln Ile Lys Ala
                205                 210                 215 ggt tac cag tct ctc aag aag att gag gac tgc atc cgc gct ggc cag    784
Gly Tyr Gln Ser Leu Lys Lys Ile Glu Asp Cys Ile Arg Ala Gly Gln
                220                 225                 230 cat ggg cga gcg ctt gtt gaa gcg tgc aat gaa ttc tac acc agg atc    832
His Gly Arg Ala Leu Val Glu Ala Cys Asn Glu Phe Tyr Thr Arg Ile
        235                 240                 245 cct cat gac ttt gga ctc tcc atc cct cca gta atc cgg aca gag aag    880
Pro His Asp Phe Gly Leu Ser Ile Pro Pro Val Ile Arg Thr Glu Lys
    250                 255                 260 gaa ctg tca gac aaa gta aaa ctg cta gag gca ttg gga gac att gaa    928
Glu Leu Ser Asp Lys Val Lys Leu Leu Glu Ala Leu Gly Asp Ile Glu
265                 270                 275                 280 att gcc ctt aaa ctg gtg aag tca gag cgc caa ggc cta gaa cac cca    976
Ile Ala Leu Lys Leu Val Lys Ser Glu Arg Gln Gly Leu Glu His Pro
                285                 290                 295 ctg gac caa cac tat aga aac cta cac tgt gct ttg cgt cct ctg gac   1024
Leu Asp Gln His Tyr Arg Asn Leu His Cys Ala Leu Arg Pro Leu Asp
            300                 305                 310 cat gaa agt aat gag ttt aag gtg att tct cag tac cta cag tct acg   1072
His Glu Ser Asn Glu Phe Lys Val Ile Ser Gln Tyr Leu Gln Ser Thr
```

```
                His Glu Ser Asn Glu Phe Lys Val Ile Ser Gln Tyr Leu Gln Ser Thr
                        315                 320                 325 cat gct cct aca cac aag gac tat act atg acc ttg ctg gat gtt ttc       1120
His Ala Pro Thr His Lys Asp Tyr Thr Met Thr Leu Leu Asp Val Phe
            330                 335                 340 gaa gta gag aag gaa ggg gag aaa gag gcc ttc agg gag gac ctt cct       1168
Glu Val Glu Lys Glu Gly Glu Lys Glu Ala Phe Arg Glu Asp Leu Pro
345                 350                 355                 360 aac agg atg ctg ctc tgg cat gga tcc agg ctg agt aac tgg gtg ggg       1216
Asn Arg Met Leu Leu Trp His Gly Ser Arg Leu Ser Asn Trp Val Gly
                365                 370                 375 atc ctg agc cac ggg ctt aga gtt gcc cca cct gag gct ccc atc aca       1264
Ile Leu Ser His Gly Leu Arg Val Ala Pro Pro Glu Ala Pro Ile Thr
            380                 385                 390 ggt tat atg ttt gga aaa gga atc tac ttt gct gac atg tcc tcc aag       1312
Gly Tyr Met Phe Gly Lys Gly Ile Tyr Phe Ala Asp Met Ser Ser Lys
        395                 400                 405 agt gcc aat tac tgc ttt gcc tct cgc cta aag aat aca gga ttg ctt       1360
Ser Ala Asn Tyr Cys Phe Ala Ser Arg Leu Lys Asn Thr Gly Leu Leu
    410                 415                 420 ctt ctg tca gag gta gct cta ggt cag tgt aat gaa cta ctg gag gcc       1408
Leu Leu Ser Glu Val Ala Leu Gly Gln Cys Asn Glu Leu Leu Glu Ala
425                 430                 435                 440 aat cct aaa gca caa gga ttg ctt cgg ggc aag cat agc acc aag ggg       1456
Asn Pro Lys Ala Gln Gly Leu Leu Arg Gly Lys His Ser Thr Lys Gly
                445                 450                 455 atg gga aag atg gct ccc agc cct gcc cac ttc atc acc ctg aat ggg       1504
Met Gly Lys Met Ala Pro Ser Pro Ala His Phe Ile Thr Leu Asn Gly
            460                 465                 470 agt aca gtg ccc tta gga cca gca agt gac aca gga att ctc aat cca       1552
Ser Thr Val Pro Leu Gly Pro Ala Ser Asp Thr Gly Ile Leu Asn Pro
        475                 480                 485 gag ggg tac acc ctc aac tac aat gag ttt att gtt tat agc ccc aac       1600
Glu Gly Tyr Thr Leu Asn Tyr Asn Glu Phe Ile Val Tyr Ser Pro Asn
    490                 495                 500 cag gtc cgt atg cga tac ctt cta aag att caa ttt aac ttc ctg cag       1648
Gln Val Arg Met Arg Tyr Leu Leu Lys Ile Gln Phe Asn Phe Leu Gln
505                 510                 515                 520 cta tgg tga atgttgatca gacaagccag agagaatata atcttcaaac aaaaaccaag    1707
Leu Trp caatattatg gttcttgaac ttttgatat tttgtttaat aaaatagtat aaatctgtc       1766

<210> SEQ ID NO 19
<211> LENGTH: 27
<212> TYPE: DNA
<213> ORGANISM: Artificial Sequence
<220> FEATURE:
<223> OTHER INFORMATION: PCR Primer

<400> SEQUENCE: 19
gatgattgag atgaagtatg acaccaa                                         27

<210> SEQ ID NO 20
<211> LENGTH: 21
<212> TYPE: DNA
<213> ORGANISM: Artificial Sequence
<220> FEATURE:
<223> OTHER INFORMATION: PCR Primer

<400> SEQUENCE: 20
actggtaacc ggccttgatt t                                               21
```

-continued

<210> SEQ ID NO 21
<211> LENGTH: 23
<212> TYPE: DNA
<213> ORGANISM: Artificial Sequence
<220> FEATURE:
<223> OTHER INFORMATION: PCR Probe

<400> SEQUENCE: 21
cgcttggaaa gctgacagtg gcg                                    23

<210> SEQ ID NO 22
<211> LENGTH: 20
<212> TYPE: DNA
<213> ORGANISM: Artificial Sequence
<220> FEATURE:
<223> OTHER INFORMATION: PCR Primer

<400> SEQUENCE: 22
ggcaaattca acggcacagt                                        20

<210> SEQ ID NO 23
<211> LENGTH: 20
<212> TYPE: DNA
<213> ORGANISM: Artificial Sequence
<220> FEATURE:
<223> OTHER INFORMATION: PCR Primer

<400> SEQUENCE: 23
gggtctcgct cctggaagct                                        20

<210> SEQ ID NO 24
<211> LENGTH: 27
<212> TYPE: DNA
<213> ORGANISM: Artificial Sequence
<220> FEATURE:
<223> OTHER INFORMATION: PCR Probe

<400> SEQUENCE: 24
aaggccgaga atgggaagct tgtcatc                                27

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ccaccgccgt tccctgatag                                        20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
accgaacacg ccgcaccggc                                        20

<210> SEQ ID NO 27
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 27
cgccgcctcg cgtgcgctca                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
cgacctagaa acacgcttgc                    20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ccgccaaagc tccggaagcc                    20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gcttatccga agactccgcc                    20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
ttggcgtact cgactcgata                    20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
caagaggcgc gcccgctctt                    20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ctctcgctgc atttcttgca                    20

```
<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
gactgcacca tgatggccat                                                    20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gtggtaccag tgtgggactt                                                    20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gagaagtggt accagtgtgg                                                    20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ccaccttcca gaagcaggag                                                    20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tcatcccacc gaagctcaga                                                    20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gtcttcttga ctttctgctg                                                    20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 40
ttccatcctg gcctttgcct                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
atactctgct gcaaagtcac                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ttggacttgg catactctgc                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
accatcttct tggacaggcg                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gatggtacca gcggtcaatc                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gcactgtact cgggccggaa                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
aggaggctga agcccttgag                                              20

<210> SEQ ID NO 47
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 47
cgccttttct ctttccttca                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
cacttcatcc actccatcca                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
aggtcgttct gagcctttag                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
cattagttga acacactttc                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ccagaaggca cttgctgctt                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ctactcggtc caagatcgcc                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
```

```
taataggcat cgctcttgaa                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
cacttggtcc aggcagtgac                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ctccttccgg ttgggtgtct                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
atttctcgga attcctttgg                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ggaatatacg gtcctgcttt                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
gagttcacag cagcaggagc                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tatctgctga agcagaggag                                              20

<210> SEQ ID NO 60
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 60
agagtcagga tcttcatgtt                                                    20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tggccttcac ttcatccttg                                                    20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
ggaagccttg ttggccgtcc                                                    20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ttcatctttt ccacctcctt                                                    20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
tccatcttct tattcatctt                                                    20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cttcctccat cttcttattc                                                    20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
ggcttccttt acttcctcca                                                    20
```

-continued

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
cggatgttgg cttcctttac                                                    20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cagacacaac tcggatgttg                                                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
gaagtcctca gacacaactc                                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
agacgtcctg gaggaagtcc                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
ctgaaggctc ttggtggagg                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ggccacaact tcaacaggct                                                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 73
tgataccttc ctccttgacc                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
agtccagaat caggatccac                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
cttcccacct ttctccagga                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
cgatgtccac caggccaagg                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ttgtcgtcct ccagaagctg                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ccaggacctg aatatccaat                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ggcatcctcc ttggacggca                                               20

<210> SEQ ID NO 80
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tttggagtgc aagcgttcc                                                   20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
ctggccatag tcaatctcca                                                  20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
tgtgagcttc ttcactgcct                                                  20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
atactttcca catcaaagat                                                  20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
atctcatact ccaccatggc                                                  20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
tatgcggcct ggatctgcct                                                  20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
```
ccaggatctg agagtcgctg                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
aggagcggag gcttcttcat                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
taggccacct cgatgtccag                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
tcgatgggat ccttgctgct                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
caaccacctt aatgtcagtt                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
ttcagaatct ctgtcaacca                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
agtgttctta acatacttcc                                              20

<210> SEQ ID NO 93
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 93
gcattcgcct tcacgctcta                                                    20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
agcaaagttg gtggtcctgg                                                    20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
tgtagcctgt cacgggcgct                                                    20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
gagaccatgt cagcgaaata                                                    20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
caacttctcc caacaggatt                                                    20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
tgcttcagtt catacatgtt                                                    20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ctgtgcttgc ccttgggtaa                                                    20
```

```
<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
ccaaaccttt gacactgtgc                                             20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
gactaatgtt agctgaagga                                             20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
acagggaggt cttaaaattg                                             20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
accgggtgtg actcggctac                                             20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
ttcataccac agccaccggg                                             20

<210> SEQ ID NO 105
<211> LENGTH: 1797
<212> TYPE: DNA
<213> ORGANISM: Homo sapiens
<220> FEATURE:
<221> NAME/KEY: CDS
<222> LOCATION: (87)...(1691)

<400> SEQUENCE: 105
aaagagttaa taatggcaac acggctccag aagactcttc ccctgccaag aaaactcgta    60
gatgccagag acaggagtcg aaaaag atg cct gtg gct gga gga aaa gct aat    113
                            Met Pro Val Ala Gly Gly Lys Ala Asn
                              1               5 aag gac agg aca gaa gac aag caa gat ggt atg cca gga agg tca tgg    161
```

```
                                                              -continued

Lys Asp Arg Thr Glu Asp Lys Gln Asp Gly Met Pro Gly Arg Ser Trp
 10              15                  20                  25 gcc agc aaa agg gtc tct gaa tct gtg aag gcc ttg ctg tta aag ggc       209
Ala Ser Lys Arg Val Ser Glu Ser Val Lys Ala Leu Leu Leu Lys Gly
             30                  35                  40 aaa gct cct gtg gac cca gag tgt aca gcc aag gtg ggg aag gct cat       257
Lys Ala Pro Val Asp Pro Glu Cys Thr Ala Lys Val Gly Lys Ala His
                 45                  50                  55 gtg tat tgt gaa gga aat gat gtc tat gat gtc atg cta aat cag acc       305
Val Tyr Cys Glu Gly Asn Asp Val Tyr Asp Val Met Leu Asn Gln Thr
         60                  65                  70 aat ctc cag ttc aac aac aac aag tac tat ctg att cag cta tta gaa       353
Asn Leu Gln Phe Asn Asn Asn Lys Tyr Tyr Leu Ile Gln Leu Leu Glu
     75                  80                  85 gat gat gcc cag agg aac ttc agt gtt tgg atg aga tgg ggc cga gtt       401
Asp Asp Ala Gln Arg Asn Phe Ser Val Trp Met Arg Trp Gly Arg Val
 90                  95                 100                 105 ggg aaa atg gga cag cac agc ctg gtg gct tgt tca ggc aat ctc aac       449
Gly Lys Met Gly Gln His Ser Leu Val Ala Cys Ser Gly Asn Leu Asn
                110                 115                 120 aag gcc aag gaa atc ttt cag aag aaa ttc ctt gac aaa acg aaa aac       497
Lys Ala Lys Glu Ile Phe Gln Lys Lys Phe Leu Asp Lys Thr Lys Asn
            125                 130                 135 aat tgg gaa gat cga gaa aag ttt gag aag gtg cct gga aaa tat gat       545
Asn Trp Glu Asp Arg Glu Lys Phe Glu Lys Val Pro Gly Lys Tyr Asp
        140                 145                 150 atg cta cag atg gac tat gcc acc aat act cag gat gaa gag gaa aca       593
Met Leu Gln Met Asp Tyr Ala Thr Asn Thr Gln Asp Glu Glu Glu Thr
    155                 160                 165 aag aaa gag gaa tct ctt aaa tct ccc ttg aag cca gag tca cag cta       641
Lys Lys Glu Glu Ser Leu Lys Ser Pro Leu Lys Pro Glu Ser Gln Leu
170                 175                 180                 185 gat ctt cgg gta cag gag tta ata aag ttg atc tgt aat gtt cag gcc       689
Asp Leu Arg Val Gln Glu Leu Ile Lys Leu Ile Cys Asn Val Gln Ala
                190                 195                 200 atg gaa gaa atg atg atg gaa atg aag tat aat acc aag aaa gcc cca       737
Met Glu Glu Met Met Met Glu Met Lys Tyr Asn Thr Lys Lys Ala Pro
            205                 210                 215 ctt ggg aag ctg aca gtg gca caa atc aag gca ggt tac cag tct ctt       785
Leu Gly Lys Leu Thr Val Ala Gln Ile Lys Ala Gly Tyr Gln Ser Leu
        220                 225                 230 aag aag att gag gat tgt att cgg gct ggc cag cat gga cga gct ctc       833
Lys Lys Ile Glu Asp Cys Ile Arg Ala Gly Gln His Gly Arg Ala Leu
    235                 240                 245 atg gaa gca tgc aat gaa ttc tac acc agg atc ccg cat gac ttt gga       881
Met Glu Ala Cys Asn Glu Phe Tyr Thr Arg Ile Pro His Asp Phe Gly
250                 255                 260                 265 ctc cgt act cct cca cta atc cgg aca cag aag gaa ctg tca gaa aaa       929
Leu Arg Thr Pro Pro Leu Ile Arg Thr Gln Lys Glu Leu Ser Glu Lys
                270                 275                 280 ata caa tta cta gag gct ttg gga gac att gaa att gct att aag ctg       977
Ile Gln Leu Leu Glu Ala Leu Gly Asp Ile Glu Ile Ala Ile Lys Leu
            285                 290                 295 gtg aaa aca gag cta caa agc cca gaa cac cca ttg gac caa cac tat      1025
Val Lys Thr Glu Leu Gln Ser Pro Glu His Pro Leu Asp Gln His Tyr
        300                 305                 310 aga aac cta cat tgt gcc ttg cgc ccc ctt gac cat gaa agt tat gag      1073
Arg Asn Leu His Cys Ala Leu Arg Pro Leu Asp His Glu Ser Tyr Glu
    315                 320                 325
```

-continued

```
ttc aaa gtg att tcc cag tac cta caa tct acc cat gct ccc aca cac    1121
Phe Lys Val Ile Ser Gln Tyr Leu Gln Ser Thr His Ala Pro Thr His
330                 335                 340                 345 agc gac tat acc atg acc ttg ctg gat ttg ttt gaa gtg gag aag gat    1169
Ser Asp Tyr Thr Met Thr Leu Leu Asp Leu Phe Glu Val Glu Lys Asp
            350                 355                 360 ggt gag aaa gaa gcc ttc aga gag gac ctt cat aac agg atg ctt cta    1217
Gly Glu Lys Glu Ala Phe Arg Glu Asp Leu His Asn Arg Met Leu Leu
365                 370                 375 tgg cat ggt tcc agg atg agt aac tgg gtg gga atc ttg agc cat ggg    1265
Trp His Gly Ser Arg Met Ser Asn Trp Val Gly Ile Leu Ser His Gly
        380                 385                 390 ctt cga att gcc cca cct gaa gct ccc atc aca ggt tac atg ttt ggg    1313
Leu Arg Ile Ala Pro Pro Glu Ala Pro Ile Thr Gly Tyr Met Phe Gly
    395                 400                 405 aaa gga atc tac ttt gct gac atg tct tcc aag agt gcc aat tac tgc    1361
Lys Gly Ile Tyr Phe Ala Asp Met Ser Ser Lys Ser Ala Asn Tyr Cys
410                 415                 420                 425 ttt gcc tct cgc cta aag aat aca gga ctg ctc tta tca gag gta       1409
Phe Ala Ser Arg Leu Lys Asn Thr Gly Leu Leu Leu Ser Glu Val
                430                 435                 440 gct cta ggt cag tgt aat gaa cta cta gag gcc aat cct aag gcc gaa    1457
Ala Leu Gly Gln Cys Asn Glu Leu Leu Glu Ala Asn Pro Lys Ala Glu
            445                 450                 455 gga ttg ctt caa ggt aaa cat agc acc aag ggg ctg ggc aag atg gct    1505
Gly Leu Leu Gln Gly Lys His Ser Thr Lys Gly Leu Gly Lys Met Ala
        460                 465                 470 ccc agt tct gcc cac ttc gtc acc ctg aat ggg agt aca gtg cca tta    1553
Pro Ser Ser Ala His Phe Val Thr Leu Asn Gly Ser Thr Val Pro Leu
    475                 480                 485 gga cca gca agt gac aca gga att ctg aat cca gat ggt tat acc ctc    1601
Gly Pro Ala Ser Asp Thr Gly Ile Leu Asn Pro Asp Gly Tyr Thr Leu
490                 495                 500                 505 aac tac aat gaa tat att gta tat aac ccc aac cag gtc cgt atg cgg    1649
Asn Tyr Asn Glu Tyr Ile Val Tyr Asn Pro Asn Gln Val Arg Met Arg
                510                 515                 520 tac ctt tta aag gtt cag ttt aat ttc ctt cag ctg tgg tga atgttgatat 1701
Tyr Leu Leu Lys Val Gln Phe Asn Phe Leu Gln Leu Trp
            525                 530 taaataaacc agagatctga tcttcaagca agaaaataag cagtgttgta cttgtgaatt 1761 ttgtgatatt ttatgtaata aaaactgtac aggtct                            1797
```

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
tcagcggccg ctgaattcta                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
ttaatgctct cgccctgccg                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
tgccattatt aactcttttg                                       20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
gtgttgccat tattaactct                                       20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
tcgactcctg tctctggcat                                       20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tctgtcctgt ccttattagc                                       20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
tggcatacca tcttgcttgt                                       20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
ctggcccatg accttcctgg                                       20

<210> SEQ ID NO 114
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 114
tcacagattc agagaccctt                      20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
ttaacagcaa ggccttcaca                      20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
ctctgggtcc acaggagctt                      20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
accttggctg tacactctgg                      20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
acaatacaca tgagccttcc                      20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
atgacatcat agacatcatt                      20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
ggagattggt ctgatttagc                      20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
atagtacttg ttgttgttga                                          20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
aacactgaag ttcctctggg                                          20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
caggctgtgc tgtcccattt                                          20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
gcctgaacaa gccaccaggc                                          20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
tggccttgtt gagattgcct                                          20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
tctttgtttc ctcttcatcc                                          20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 127
tctcgatctt cccaattgtt                                               20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
taagagattc ctctttcttt                                               20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
tttccaggca ccttctcaaa                                               20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
catctgtagc atatcatatt                                               20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
gtattggtgg catagtccat                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
tagctgtgac tctggcttca                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
tattaactcc tgtacccgaa                                               20

<210> SEQ ID NO 134
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 134
tgaacattac agatcaactt                                                 20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
tgccttgatt tgtgccactg                                                 20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ggatcctggt gtagaattca                                                 20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
tcttcttaag agactggtaa                                                 20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
gagtccaaag tcatgcggga                                                 20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
cgaatacaat cctcaatctt                                                 20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
```
tcgtccatgc tggccagccc                                                    20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
gcatgcttcc atgagagctc                                                    20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
tcctggtgta gaattcattg                                                    20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
ggaatcctgg tgtagaattc                                                    20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
gtccggatta gtggaggagt                                                    20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
ttctgacagt tccttctgtg                                                    20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
ttcaccagct taatagcaat                                                    20

<210> SEQ ID NO 147
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 147
cataactttc atggtcaagg                                                 20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
ggaaatcact ttgaactcat                                                 20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
ctatagtgtt ggtccaatgg                                                 20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
gcaaggcaca atgtaggttt                                                 20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
tcgtaacttt catggtcaag                                                 20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
ctttgaactc gtaactttca                                                 20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
ggaaatcact ttgaactcgt                                                 20
```

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
ttgtaggtac tgggaaatca                           20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
ggagcatggg tagattgtag                           20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
agcaaggtca tggtatagtc                           20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
accatccttc tccacttcaa                           20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
gaaggcttct ttctcaccat                           20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
catcctgtta tgaaggtcct                           20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 160
tgtgatggga gcttcaggtg                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
accatgccat agaagcatcc                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
cccagttact catcctggaa                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
ccatggctca agattcccac                                              20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
gtgggcaatt cgaagcccat                                              20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
agcaaagtag attcctttcc                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
cttggaagac atgtcagcaa                                              20

<210> SEQ ID NO 167
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
gcaaagcagt aattggcact                                               20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
attctttagg cgagaggcaa                                               20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
agcagcagtc ctgtattctt                                               20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
acctagagct acctctgata                                               20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
tagtagttca ttacactgac                                               20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
aggattggcc tctagtagtt                                               20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
```

```
agcaatcctt cggccttagg                                            20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
gggagccatc ttgcccagcc                                            20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
ctcccattca gggtgacgaa                                            20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
ggtcctaatg gcactgtact                                            20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
cagaattcct gtgtcacttg                                            20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
agttgagggt ataaccatct                                            20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
atatcaacat tcaccacagc                                            20

<210> SEQ ID NO 180
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 180
gatctctggt ttatttaata                                              20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
ttaaaaggta ccgcatacgg                                              20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
agatcaacat tcaccacagc                                              20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
ttgaagatca gatctctggt                                              20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
caagtacaac actgcttatt                                              20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
tattacataa aatatcacaa                                              20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
gcactcgcct tccagagcct                                              20
```

```
<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187
ttcatttagc actcgccttc                                               20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188
attatcaact ttcttggctt                                               20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
ctgttgcttt gttgccatta                                               20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
gagagtcgtc ttctgttgct                                               20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
cttcttgcca ggaggagagt                                               20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
ggcacgtgcg catcttcttg                                               20

<210> SEQ ID NO 193
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 193
ttccctccag ccataggccc                                        20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
ctcgattgtc ttttgtcctg                                        20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
ggtcttcaca gagtctcgat                                        20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
cctttaacag caaggtcttc                                        20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
tttcccagct tggctgcaca                                        20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
atctccttca caatacacat                                        20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
atttagcatg acatcataga                                        20

```
<210> SEQ ID NO 200
<211> LENGTH: 20
<212> TYPE: DNA<220>
<213> ORGANISM: Artificial Sequence
<220> FEATURE:
<223> OTHER INFORMATION: Antisense Oligonucleotide

<400> SEQUENCE: 200
tgttgttgaa ctggagattg                                            20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
agctgaataa ggtagtactt                                            20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202
tcctctgggc atcatcttct                                            20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
cacctcatcc aaacactgaa                                            20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
gccccgtctt tccaactcgg                                            20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
agaacaagtc accaagctgt                                            20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 206
cttttgcttt gttgaggtca                                               20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
ctcacggtcc tcccaattgt                                               20

<210> SEQ ID NO 208
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 208
tgtaacatgt cgtattttcc                                               20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
cgtgctggca gcatagtcca                                               20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
tcttttgttt tactttcatc                                               20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
actcaggctt caaagtttcc                                               20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
ctggactcga agatccagct                                               20

<210> SEQ ID NO 213
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 213
acagatcaac tttagcagct                                          20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
atttcttcca tggtctgcac                                          20

<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
gtcatacttc atctcaatca                                          20

<210> SEQ ID NO 216
<211> LENGTH: 20
<212> TYPE: DNA<220>
<213> ORGANISM: Artificial Sequence
<220> FEATURE:
<223> OTHER INFORMATION: Antisense Oligonucleotide

<400> SEQUENCE: 216
tttgcgccac tgtcagcttt                                          20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
gagagactgg taaccggcct                                          20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
ggatgcagtc ctcaatcttc                                          20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219
```
ctcgcccatg ctggccagcg                    20

<210> SEQ ID NO 220
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220
attgcacgct tcaacaagcg                    20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221
agggatcctg gtgtagaatt                    20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222
atggagagtc caaagtcatg                    20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
ctgtccggat tactggaggg                    20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
ttgtctgaca gttccttctc                    20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
cctctagcag ttttactttg                    20

<210> SEQ ID NO 226
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 226
aatttcaatg tctcccaatg                                               20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
gacttcacca gtttaagggc                                               20

<210> SEQ ID NO 228
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 228
gttctaggcc ttggcgctct                                               20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
atagtgttgg tccagtgggt                                               20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
caaagcacag tgtaggtttc                                               20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
ctttcatggt ccagaggacg                                               20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232
aaatcacctt aaactcatta                                               20
```

```
<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 233
cgtagactgt aggtactgag                                          20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234
gtccttgtgt gtaggagcat                                          20

<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235
atccagcaag gtcatagtat                                          20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236
tccttctcta cttcgaaaac                                          20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
tgaaggcctc tttctcccct                                          20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
cctgttagga aggtcctccc                                          20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 239
atccatgcca gagcagcatc                                              20

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240
ccagttactc agcctggatc                                              20

<210> SEQ ID NO 241
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 241
ccgtggctca ggatccccac                                              20

<210> SEQ ID NO 242
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 242
cctgtgatgg gagcctcagg                                              20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243
tccttttcca aacatataac                                              20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244
gacatgtcag caaagtagat                                              20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245
cagtaattgg cactcttgga                                              20

<210> SEQ ID NO 246

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 246
ttctttaggc gagaggcaaa                                                  20

<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247
cagaagaagc aatcctgtat                                                  20

<210> SEQ ID NO 248
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 248
tgacctagag ctacctctga                                                  20

<210> SEQ ID NO 249
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 249
cctccagtag ttcattacac                                                  20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250
cttgtgcttt aggattggcc                                                  20

<210> SEQ ID NO 251
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 251
gcttgccccg aagcaatcct                                                  20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252
```
tcccatcccc ttggtgctat                                               20

<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 253
gcagggctgg gagccatctt                                               20

<210> SEQ ID NO 254
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 254
ttcagggtga tgaagtgggc                                               20

<210> SEQ ID NO 255
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 255
aagggcactg tactcccatt                                               20

<210> SEQ ID NO 256
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 256
gtgtcacttg ctggtcctaa                                               20

<210> SEQ ID NO 257
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 257
cctctggatt gagaattcct                                               20

<210> SEQ ID NO 258
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 258
ttgtagttga gggtgtaccc                                               20

<210> SEQ ID NO 259
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 259
gggctataaa caataaactc                                          20

<210> SEQ ID NO 260
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 260
tgaatcttta gaaggtatcg                                          20

<210> SEQ ID NO 261
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 261
atagctgcag gaagttaaat                                          20

<210> SEQ ID NO 262
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 262
gtctgatcaa cattcaccat                                          20

<210> SEQ ID NO 263
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 263
attatattct ctctggcttg                                          20

<210> SEQ ID NO 264
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 264
caagaaccat aatattgctt                                          20

<210> SEQ ID NO 265
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 265
ttatactatt ttattaaaca                                          20
```

<210> SEQ ID NO 266
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 266
aggcgtgaat tagggagaga                                              20

<210> SEQ ID NO 267
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 267
tgagcctcag gcgtgaatta                                              20

<210> SEQ ID NO 268
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 268
gtctagcaac tctccatgag                                              20

<210> SEQ ID NO 269
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 269
ctggctgcca cccggcctgg                                              20

<210> SEQ ID NO 270
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 270
acatgggaga ggtcctggct                                              20

<210> SEQ ID NO 271
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 271
gagccatggc tgtcccaaga                                              20

<210> SEQ ID NO 272
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 272
tgtacccagg gcttcggctt                    20

<210> SEQ ID NO 273
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 273
cagggccctc agtctgtacc                    20

<210> SEQ ID NO 274
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 274
ttcctgcctg ccggcccttc                    20

<210> SEQ ID NO 275
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 275
ctcagcggtg gagcggaagg                    20

<210> SEQ ID NO 276
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 276
tctgcgggta tggccttgag                    20

<210> SEQ ID NO 277
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 277
gattatgcgc ttctctgcgg                    20

<210> SEQ ID NO 278
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 278
agtggacatg ttggatccac                    20

<210> SEQ ID NO 279
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 279
gtagtcctca tacacctggg                                              20

<210> SEQ ID NO 280
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 280
cgatgttggt ctggttcagg                                              20

<210> SEQ ID NO 281
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 281
ttgttgttgt tctcgatgtt                                              20

<210> SEQ ID NO 282
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 282
tggatgatgt agaacttctt                                              20

<210> SEQ ID NO 283
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 283
agcggttgct gtcttggagc                                              20

<210> SEQ ID NO 284
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 284
ccccagcggt tccagcaggt                                              20

<210> SEQ ID NO 285
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 285
ccgacctctc ccacacggcc                                          20

<210> SEQ ID NO 286
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 286
ttgactggcc gacctctccc                                          20

<210> SEQ ID NO 287
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 287
agtggttgat ctttgactgg                                          20

<210> SEQ ID NO 288
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 288
agccttgtga agtggttgat                                          20

<210> SEQ ID NO 289
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 289
ctcaaagtcc ttctttgcat                                          20

<210> SEQ ID NO 290
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 290
ttttcccgaa atttcttctc                                          20

<210> SEQ ID NO 291
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 291
ccgctctgcc cagttgttct                                          20

<210> SEQ ID NO 292
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 292
cttgcccggg tgagacacaa                                               20

<210> SEQ ID NO 293
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 293
cttcgataag tgtgtacttg                                               20

<210> SEQ ID NO 294
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 294
ggcctcatcc tctgcctgta                                               20

<210> SEQ ID NO 295
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 295
tctgtccacc ttcaccacag                                               20

<210> SEQ ID NO 296
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 296
ttagtcacag tcctcactgg                                               20

<210> SEQ ID NO 297
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 297
gagcagggct gcacccgctt                                               20

<210> SEQ ID NO 298
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 298
```
ttctgcgtgg ctgggtccag                                          20

<210> SEQ ID NO 299
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 299
tgttagtgat gagcttctgc                                          20

<210> SEQ ID NO 300
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 300
cttgaacatc tccttgctga                                          20

<210> SEQ ID NO 301
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 301
ggccatggtg ttcttgaaca                                          20

<210> SEQ ID NO 302
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 302
ttcttcacat ccaggtccat                                          20

<210> SEQ ID NO 303
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 303
tgcttgctca gctttcccag                                          20

<210> SEQ ID NO 304
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 304
aaaccccgtg caatctgttg                                          20

<210> SEQ ID NO 305
<211> LENGTH: 20
<212> TYPE: DNA
<213> ORGANISM: Artificial Sequence -continued

```
<220> FEATURE:
<223> OTHER INFORMATION: Antisense Oligonucleotide

<400> SEQUENCE: 305
cctccagcgc ctccaaggcc                                          20

<210> SEQ ID NO 306
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 306
ggcctttcag ggcctcctcc                                          20

<210> SEQ ID NO 307
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 307
gctttggcca ccatccgtgg                                          20

<210> SEQ ID NO 308
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 308
aagtgtgagg acagctcctc                                          20

<210> SEQ ID NO 309
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 309
ttgtgcggga tgacggtgta                                          20

<210> SEQ ID NO 310
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 310
ctgtggccga agttgtgcgg                                          20

<210> SEQ ID NO 311
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 311
ttggcctgca gaagctcagg                                          20
```

```
<210> SEQ ID NO 312
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 312
gccagcacca gcagcatgtc                                               20

<210> SEQ ID NO 313
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 313
ggccagctcg atgtccgcca                                               20

<210> SEQ ID NO 314
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 314
accgtcttct cctgctcaga                                               20

<210> SEQ ID NO 315
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 315
gtggcacctc ctccaccgtc                                               20

<210> SEQ ID NO 316
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 316
gctggtagtc tcggtccagg                                               20

<210> SEQ ID NO 317
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 317
ctagcagctg cagctggcac                                               20

<210> SEQ ID NO 318
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 318
tcaggtgctc cagagtctag					20

<210> SEQ ID NO 319
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 319
gtatcacctt gtactcaggt					20

<210> SEQ ID NO 320
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 320
gccagtctgt tctaagtagg					20

<210> SEQ ID NO 321
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 321
gggcacctgt ggttgctgcc					20

<210> SEQ ID NO 322
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 322
tccagatgtg ttgaagtgta					20

<210> SEQ ID NO 323
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 323
gaatctgtct tcctcccctt					20

<210> SEQ ID NO 324
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 324
ccgattaccc agtttggagt					20

<210> SEQ ID NO 325

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 325
ccatgttggt gccatgccac                                                20

<210> SEQ ID NO 326
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 326
ccactagtga ggatggcggc                                                20

<210> SEQ ID NO 327
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 327
ccaccagaat gtggcatgat                                                20

<210> SEQ ID NO 328
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 328
tgaggcaaag tagatgccct                                                20

<210> SEQ ID NO 329
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 329
catgccaata acatatccag                                                20

<210> SEQ ID NO 330
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 330
atgtagccga catggtgggc                                                20

<210> SEQ ID NO 331
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 331
```
tatggtgctc tctgcccagg                                           20

<210> SEQ ID NO 332
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 332
ggttgtccgt gttgatatgg                                           20

<210> SEQ ID NO 333
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 333
gaggtgggct cttcaagctg                                           20

<210> SEQ ID NO 334
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 334
tggcctcggg caatgacact                                           20

<210> SEQ ID NO 335
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 335
caactcagtg tcctgggtcg                                           20

<210> SEQ ID NO 336
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 336
ggcaccacca cttgctggcc                                           20

<210> SEQ ID NO 337
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 337
gcagggcaca ggctggccct                                           20

<210> SEQ ID NO 338
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 338
gctgctgaac tctgggcagg                                              20

<210> SEQ ID NO 339
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 339
tagatgaggt actcgctctg                                              20

<210> SEQ ID NO 340
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 340
aggtagcgca ggcgacactg                                              20

<210> SEQ ID NO 341
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 341
gcactcagag gtggacctcc                                              20

<210> SEQ ID NO 342
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 342
ccagccttgc aggaccccgg                                              20

<210> SEQ ID NO 343
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 343
atgattgaag atcacagtcc                                              20

<210> SEQ ID NO 344
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 344
accagagatg ggcaggatga                                              20
```

```
<210> SEQ ID NO 345
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 345
caacgtattg tattcttgaa                                              20
```

ANTISENSE MODULATION OF PARP EXPRESSION

FIELD OF THE INVENTION

The present invention provides compositions and methods for modulating the expression of Poly (ADP-ribose) polymerase (PARP). In particular, this invention relates to antisense compounds, particularly oligonucleotides, specifically hybridizable with nucleic acids encoding human PARP. Such oligonucleotides have been shown to modulate the expression of PARP.

BACKGROUND OF THE INVENTION

Posttranslational modifications of proteins are required for many cellular functions including the mediation of protein—protein interactions, enzymatic activity, protein degradation, localization of proteins to cellular compartments and maintenance of protein stability.

Poly (ADP-ribosylation) is a posttranslational modification of nuclear proteins whereby molecules of ADP-ribose are added to acceptor proteins to form branched polymers. The attachment of these polymers to nuclear proteins, which is dependent on the presence of DNA strand breaks, converts the DNA ends into intracellular signals that modulate DNA repair and cell survival programs. ADP-ribosylation, therefore, plays an important role in many cellular processes including chromatin decondensation, DNA replication, DNA repair, gene expression, malignant transformation, cellular differentiation and apoptosis (D'Amours et al., Biochem. J., 1999, 342, 249–268; Pieper et al., Trends Pharmacol. Sci., 1999, 20, 171–181).

The enzymes that catalyze the formation of poly (ADP-ribose) polymers, poly (ADP-ribose) polymerases, also known as PARPS, constitute a gene family with three known members identified to date; PARP, PARP-2 and PARP-3 (Ame et al., J. Biol. Chem., 1999, 274, 17860–17868; Cherney et al., Proc. Natl. Acad. Sci. U.S.A., 1987, 84, 8370–8374; Johansson, Genomics, 1999, 57, 442–445).

All three members of the PARP family are ubiquitously expressed in all tissues and cell lines examined (Alkhatib et al., Proc. Natl. Acad. Sci. U.S.A., 1987, 84, 1224–1228; Ame et al., J. Biol. Chem., 1999, 274, 17860–17868; Johansson, Genomics, 1999, 57, 442–445). Characterization of the PARP proteins revealed a three-domain structure for PARP-1, having a DNA binding domain, an automodification domain and a catalytic domain (Cherney et al., Proc. Natl. Acad. Sci. U.S.A., 1987, 84, 8370–8374). PARP-2 and PARP-3 lack the first two domains and consist primarily of the catalytic domain which contains the NAD binding site in all three proteins (Ame et al., J. Biol. Chem., 1999, 274, 17860–17868; Johansson, Genomics, 1999, 57, 442–445). Functionally, however, PARP-1 has been the best characterized of the three PARPS.

Mice lacking the PARP-1 gene show normal fetal and postnatal development but have inherent genomic instability and are highly sensitive to DNA damage induced by radiation and alkylating agents (Trucco et al., Mol. Cell. Biochem., 1999, 193, 53–60). These mice also demonstrated downregulation and lack of responsiveness of p53 protein to genotoxins (Althaus et al., Mol. Cell. Biochem., 1999, 193, 5–11). p53 is induced by a variety of apoptotic stimuli and is required for apoptosis in many cell systems and recently it was shown that PARP-1 binds to p53 and alters its DNA binding properties (Malanga et al., J. Biol. Chem., 1998, 273, 11839–11843). These results support a role for the PARP enzymes in the regulation of programmed cell death, or apoptosis.

Other studies of knockout mice implicate PARP in the development of the inflammatory response. Oliver et al. showed that PARP-1 deficient mice were extremely resistant to LPS-induced endotoxic shock due to a defect in NFkB transcriptional activation with the consequence of attenuating systemic inflammatory processes (Oliver et al., Embo J., 1999, 18, 4446–4454). In addition, the combination therapy of nicotinic acid, a PARP inhibitor, and thalidomide, a TNF-alpha inhibitor, caused a powerful synergistic inhibition of arthritis in male DBA/I hybrid mice suffering from type II collagen-induced arthritis (Kroger et al., Inflammation, 1996, 20, 203–215; Miesel et al., Inflammation, 1995, 19, 379–387).

MPTP is a neurotoxin that causes parkinsonism in humans and animals, and mice lacking the PARP-1 gene are dramatically spared from MPTP-induced neurotoxicity. This study indicates that limiting PARP activity represents a potential therapeutic target for the reduction of dopaminergic neuronal loss (Mandir et al., Proc. Natl. Acad. Sci. U.S.A., 1999, 96, 5774–5779). Other neurologic conditions associated with the activation of PARP include meningitis-associated intracranial complications and ischemia (Koedel and Pfister, Brain Pathol., 1999, 9, 57–67; Love, Brain Pathol., 1999, 9, 119–131).

PARP knockout mice have also been studied in the context of the development of diabetes. Burkhart et al. have shown that mice lacking the PARP-1 gene are completely resistant to the development of diabetes induced by the beta-cell toxin, streptozocin (Burkart et al., Nat. Med., 1999, 5, 314–319).

The pharmacological modulation of PARP activity and/or expression may therefore be an appropriate point of therapeutic intervention in pathological conditions such as diabetes, cancer, cellular injury resulting from oxidative stress and inflammatory conditions.

To date, investigative strategies aimed at modulating PARP function have involved the use of antibodies (Duriez et al., Biochim. Biophys. Acta., 1997, 1334, 65–72; Prasad et al., Electrophoresis, 1999, 20, 618–625), inhibitory peptides and peptidomimetics including trans-dominant inhibition by the DNA binding domain of the protein (Kupper et al., Cancer Res., 1996, 56, 2715–2717; Molinete et al., Embo J., 1993, 12, 2109–2117), small molecule inhibitors (Gale, J. Pediatr. Endocrinol. Metab., 1996, 9, 375–379; Richardson et al., Adv. Exp. Med. Biol., 1999, 457, 267–279; Sheng et al., Cancer Detect. Prev., 1998, 22, 284–292; Shiokawa et al., FEBS Lett., 1997, 413, 99–103; Weltin et al., Int. J. Radiat. Biol., 1997, 72, 685–692), antisense expression vectors (Simbulan-Rosenthal et al., Biochemistry, 1998, 37, 9363–9370; Simbulan-Rosenthal et al., Biochem. Biophys. Res. Comm., 1998, 253, 864–868; Simbulan-Rosenthal et al., Biochemistry, 1996, 35, 11622–11633; Simbulan-Rosenthal et al., J. Biol. Chem., 1998, 273, 13703–13712; Simbulan-Rosenthal et al., Mol. Cell. Biochem., 1999, 193, 137–148) and gene knock-outs in mice (Althaus et al., Mol. Cell. Biochem., 1999, 193, 5–11; Burkart et al., Nat. Med., 1999, 5, 314–319; Mandir et al., Proc. Natl. Acad. Sci. U.S.A., 1999, 96, 5774–5779; Oliver et al., Embo J., 1999, 18, 4446–4454; Trucco et al., Mol. Cell. Biochem., 1999, 193, 53–60).

Currently, there are no known therapeutic agents that effectively inhibit the synthesis of PARP and consequently, there remains a long felt need for these.

Antisense technology is emerging as an effective means for reducing the expression of specific gene products and may therefore prove to be uniquely useful in a number of therapeutic, diagnostic, and research applications for the modulation of PARP expression.

The present invention provides compositions and methods for modulating human PARP expression, including that of PARP-1, PARP-2 and/or PARP-3.

SUMMARY OF THE INVENTION

The present invention is directed to antisense compounds, particularly oligonucleotides, which are targeted to a nucleic acid encoding human PARP, and which modulate the expression of human PARP. Pharmaceutical and other compositions comprising the antisense compounds of the invention are also provided. Further provided are methods of modulating the expression of PARP in human cells or tissues comprising contacting said cells or tissues with one or more of the antisense compounds or compositions of the invention. Further provided are methods of treating a human suspected of having or being prone to a disease or condition associated with expression of PARP by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding PARP, ultimately modulating the amount of PARP produced. This is accomplished by providing antisense compounds which specifically hybridize with one or more nucleic acids encoding PARP. As used herein, the terms "target nucleic acid" and "nucleic acid encoding PARP" encompass DNA encoding PARP, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of PARP. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding PARP. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding PARP, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intronexon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e. from about 8 to about 30 linked nucleosides). Particularly preferred antisense compounds are antisense oligonucleotides, even more preferably those comprising from about 12 to about 25 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thiono-alkylphosphonates, thionoalkylphosphotriesters, and borano-phosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863;

4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—$CH_2CH_2OCH_3$, also known as 2'—O—(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O-$CH_2$—O—$CH_2$—N($CH_2$)$_2$, also described in examples hereinbelow.

Other preferred modifications include 2'-methoxy (2'—O—$CH_3$), 2'-aminopropoxy (2'—O$CH_2CH_2CH_2NH_2$) and 2'-fluoro (2-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And*

Engineering, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of PARP is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding PARP, enabling sandwich and other assays to easily be constructed to exploit this fact. Hybridization of the antisense oligonucleotides of the invention with a nucleic acid encoding PARP can be detected by means known in the art. Such means may include conjugation of an enzyme to the oligonucleotide, radiolabelling of the oligonucleotide or any other suitable detection means. Kits using such detection means for detecting the level of PARP in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and triglycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside G. or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}$ 15G, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ ualkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (so dium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham MA or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3' phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3' phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHC_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 ML, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) Nucleoside Amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1 M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness . The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol ), 4,4'-dimethoxytrityl chloride (880 mg, 2.60 mmol ) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol ) was co-evaporated with toluene (20 mL). To the residue N,N-diisopropylamine tetrazonide (0.29 g, 1.67 mmol ) was added and dried over $P_2O_5$ under high vacuum overnight at 40° C. Then the reaction mixture was dissolved in anhydrous acetonitrile (8.4mL) and 2-cyanoethyl-$N,N,N^1,N^1$-tetraisopropylphosphoramidite (2.12 mL, 6.08 mmol ) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-Dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$-O—$CH_2$—$N(CH_3)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol ) with stirring in a 100 mL bomb. Hydrogen gas evolves as the solid dissolves. $O_2$-,2'-anhydro-5-methyluridine (1.2 g, 5 mmol ), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl Uridine

To 0.5 g (1.3 mmol ) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. , 5,508,270, herein incorporated by reference.

Alkyl phosphonate oligonucleotides are prepared as described in U.S. Pat. No. , 4,469,863, herein incorporated by reference.

3'-Deoxy-3'-methylene phosphonate oligonucleotides are prepared as described in U.S. Pat. Nos., 5,610,289 or 5,625,050, herein incorporated by reference.

Phosphoramidite oligonucleotides are prepared as described in U.S. Pat. No. , 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O-Me]Chimeric Phosphorothioate Oligonucleotides

Chimeric oligonucleotides having 2'-O-alkyl phosphorothioate and 2'-deoxy phosphorothioate oligo-nucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphor-amidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]--[21-deoxy]--[2'-O-(Methoxyethyl)]Chimeric Phosphorothioate Oligonucleotides

[2'-O-(2-methoxyethyl)]--[2'-deoxy]--[-2'-O-(methoxyethyl)] chimeric phosphorothioate oligonucleotides were prepared as per the procedure above for the 2'-methyl chimeric oligonucleotide, with the substitution of 2'-O-(methoxyethyl) amidites for the 2'-O-methyl amidites.

[2'-O-(2-Nethoxyethyl)Phosphodiester]--[2'-deoxy Phosphorothioate]--[2'-O-(2-Methoxyethyl) Phosphodiester]Chimeric Oligonucleotides

[2'-O-(2-methoxyethyl phosphodiester]--[2'-deoxy phosphorothioate]--[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Califa., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va. T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

3T3-L1 Cells:

The mouse embryonic adipocyte-like cell line 3T3-L1 was obtained from the American Type Culure Collection (Manassas, Va.). 3T3-L1 cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 80% confluence. Cells were seeded into 96-well plates (Falcon-Primaria #3872) at a density of 4000 cells/well for use in RT-PCR analysis.

Treatment with Antisense Compounds:

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 containing 3.75 µg/mL LIPO-FECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of PARP Expression

Antisense modulation of PARP expression can be assayed in a variety of ways known in the art. For example, PARP mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed as multiplexable. Other methods of PCR are also known in the art.

Protein levels of PARP can be quantitated in a variety of ways well known in the art, such as immunoprecipitation, Western blot analysis (immunoblotting), ELISA or fluorescence-activated cell sorting (FACS). Antibodies directed to PARP can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., Clin. Chem., 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total mRNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of PARP mRNA Levels

Quantitation of PARP mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 μL PCR cocktail (1×TAQMAN™ buffer A, 5.5 MM MgCl$_2$, 300 μM each of DATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL poly(A) mRNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Probes and primers to human PARP-1 were designed to hybridize to a human PARP-1 sequence, using published sequence information (GenBank accession number M32721, incorporated herein as SEQ ID NO:3). For human PARP-1 the PCR primers were:

forward primer: CCTGATCCCCCACGACTTT (SEQ ID NO: 4)

reverse primer: CACCTTGGCCTGCACACTG (SEQ ID NO: 5) and the PCR probe was: FAM-AAGCCTCCGCTCCTGAACAATGCA-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye.

Probes and primers to human PARP-2 were designed to hybridize to a human PARP-2 sequence, using published sequence information (GenBank accession number AF085734, incorporated herein as SEQ ID NO:7). For human PARP-2 the PCR primers were:

forward primer: AGAAGACTCTTCCCCTGCCAA (SEQ ID NO: 8)

reverse primer: CCTCCAGCCACAGGCATCT (SEQ ID NO: 9) and the PCR probe was: FAM-AAACTCGTAGATGCCAGAGACAGGAGTCGA-TAMRA (SEQ ID NO: 10) where FAM (PE-Applied Biosystems, Foster City, Calif.) is the fluorescent reporter dye) and TAMRA (PE-Applied Biosystems, Foster City, Calif.) is the quencher dye.

Probes and primers to human PARP-3 were designed to hybridize to a human PARP-3 sequence, using published sequence information (GenBank accession number AF083068, incorporated herein as SEQ ID NO:11). For human PARP-3 the PCR primers were:

forward primer: CCTCATGGACCTGGATGTGAA (SEQ ID NO: 12)

reverse primer: GAAACCCCGTGCAATCTGTT (SEQ ID NO: 13) and the PCR probe was: FAM-ATGCCCCTGGGAAAGCTGAGCAAG-TAMRA (SEQ ID NO: 14) where FAM (PE-Applied Biosystems, Foster City, Calif.) is the fluorescent reporter dye) and TAMRA (PE-Applied Biosystems, Foster City, Calif.) is the quencher dye.

For human GAPDH the PCR primers were:

forward primer: GAAGGTGAAGGTCGGAGTC (SEQ ID NO: 15)

reverse primer: GAAGATGGTGATGGGATTTC (SEQ ID NO: 16) and the PCR probe was: 5' JOE-CAAGCTTCCCGTTCTCAGCC-TAMRA 3' (SEQ ID NO: 17) where JOE (PE-Applied Biosystems, Foster City, Calif.) is the fluorescent reporter dye) and TAMRA (PE-Applied Biosystems, Foster City, Calif.) is the quencher dye.

Probes and primers to mouse PARP-2 were designed to hybridize to a mouse PARP-2 sequence, using published sequence information (GenBank accession number AF072521, incorporated herein as SEQ ID NO:18). For mouse PARP-2 the PCR primers were:

forward primer: GATGATTGAGATGAAGTATGACAC-CAA (SEQ ID NO:19)

reverse primer: ACTGGTAACCGGCCTTGATTT (SEQ ID NO: 20) and the PCR probe was: FAM-CGCTTGGAAAGCTGACAGTGGCG-TAMRA (SEQ ID NO: 21) where FAM (PE-Applied Biosystems, Foster City, Calif.) is the fluorescent reporter dye) and TAMRA (PE-Applied Biosystems, Foster City, Calif.) is the quencher dye.

For mouse GAPDH the PCR primers were:

forward primer: GGCAAATTCAACGGCACAGT (SEQ ID NO: 22)

reverse primer: GGGTCTCGCTCCTGGAAGCT (SEQ ID NO: 23) and the PCR probe was: 5' JOE-AAGGCCGAGAATGGGAAGCTTGTCATC-TAMRA 3' (SEQ ID NO: 24) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of PARP mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human PARP-1, a human PARP-1 specific probe was prepared by PCR using the forward primer CCTGATC-CCCCACGACTTT (SEQ ID NO: 4) and the reverse primer CACCTTGGCCTGCACACTG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human PARP Expression by Chimeric Phosphorothioate Oligonucleotides having 2'-MOE Wings and a Deoxy Gap In accordance with the present invention, a series of oligonucleotides were designed to target different regions of the human PARP-1 RNA, using published sequences (GenBank accession number M32721, incorporated herein as SEQ ID NO: 3). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human PARP-1 mRNA levels by quantitative real-time PCR as described in other examples herein. Data are averages from two experiments. If present, "N.D." indicates "no data".

TABLE 1

Inhibition of human PARP-1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 125965 | 5'UTR | 3 | 4 | ccaccgccgttccctgatag | 39 | 25 |
| 125966 | 5'UTR | 3 | 23 | accgaacacgccgcaccggc | 40 | 26 |
| 125967 | 5'UTR | 3 | 74 | cgccgcctcgcgtgcgctca | 0 | 27 |
| 125968 | 5'UTR | 3 | 99 | cgacctagaaacacgcttgc | 45 | 28 |
| 125969 | 5'UTR | 3 | 127 | ccgccaaagctccggaagcc | 53 | 29 |
| 125970 | Start Codon | 3 | 162 | gcttatccgaagactccgcc | 75 | 30 |
| 125971 | Coding | 3 | 184 | ttggcgtactcgactcgata | 0 | 31 |
| 125972 | Coding | 3 | 202 | caagaggcgcgcccgctctt | 29 | 32 |
| 125973 | Coding | 3 | 220 | ctctcgctgcatttcttgca | 0 | 33 |
| 125974 | Coding | 3 | 262 | gactgcaccatgatggccat | 47 | 34 |

TABLE 1-continued

Inhibition of human PARP-1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 125975 | Coding | 3 | 299 | gtggtaccagtgtgggactt | 0 | 35 |
| 125976 | Coding | 3 | 304 | gagaagtggtaccagtgtgg | 45 | 36 |
| 125977 | Coding | 3 | 321 | ccaccttccagaagcaggag | 51 | 37 |
| 125978 | Coding | 3 | 382 | tcatcccaccgaagctcaga | 39 | 38 |
| 125979 | Coding | 3 | 403 | gtcttcttgacttctgctg | 60 | 39 |
| 125980 | Coding | 3 | 444 | ttccatcctggcctttgcct | 33 | 40 |
| 125981 | Coding | 3 | 491 | atactctgctgcaaagtcac | 56 | 41 |
| 125982 | Coding | 3 | 502 | ttggacttggcatactctgc | 36 | 42 |
| 125983 | Coding | 3 | 571 | accatcttcttggacaggcg | 77 | 43 |
| 125984 | Coding | 3 | 618 | gatggtaccagcggtcaatc | 1 | 44 |
| 125985 | Coding | 3 | 673 | gcactgtactcgggccggaa | 29 | 45 |
| 125986 | Coding | 3 | 700 | aggaggctgaagcccttgag | 0 | 46 |
| 125987 | Coding | 3 | 771 | cgccttttctctttccttca | 11 | 47 |
| 125988 | Coding | 3 | 797 | cacttcatccactccatcca | 49 | 48 |
| 125989 | Coding | 3 | 871 | aggtcgttctgagcctttag | 0 | 49 |
| 125990 | Coding | 3 | 918 | cattagttgaacacactttc | 0 | 50 |
| 125991 | Coding | 3 | 964 | ccagaaggcacttgctgctt | 27 | 51 |
| 125992 | Coding | 3 | 990 | ctactcggtccaagatcgcc | 32 | 52 |
| 125993 | Coding | 3 | 1069 | taataggcatcgctcttgaa | 64 | 53 |
| 125994 | Coding | 3 | 1102 | cacttggtccaggcagtgac | 41 | 54 |
| 125995 | Coding | 3 | 1136 | ctccttccggttgggtgtct | 49 | 55 |
| 125996 | Coding | 3 | 1165 | atttctcggaattccttgg | 28 | 56 |
| 125997 | Coding | 3 | 1212 | ggaatatacggtcctgcttt | 47 | 57 |
| 125998 | Coding | 3 | 1285 | gagttcacagcagcaggagc | 42 | 58 |
| 125999 | Coding | 3 | 1302 | tatctgctgaagcagaggag | 59 | 59 |
| 126000 | Coding | 3 | 1333 | agagtcaggatcttcatgtt | 50 | 60 |
| 126001 | Coding | 3 | 1371 | tggccttcacttcatccttg | 33 | 61 |
| 126002 | Coding | 3 | 1421 | ggaagccttgttggccgtcc | 20 | 62 |
| 126003 | Coding | 3 | 1459 | ttcatcttttccacctcctt | 54 | 63 |
| 126004 | Coding | 3 | 1471 | tccatcttcttattcatctt | 24 | 64 |
| 126005 | Coding | 3 | 1476 | cttcctccatcttcttattc | 26 | 65 |
| 126006 | Coding | 3 | 1487 | ggcttccttacttcctcca | 26 | 66 |
| 126007 | Coding | 3 | 1495 | cggatgttggcttccttac | 55 | 67 |
| 126008 | Coding | 3 | 1506 | cagacacaactcggatgttg | 52 | 68 |
| 126009 | Coding | 3 | 1514 | gaagtcctcagacacaactc | 6 | 69 |
| 126010 | Coding | 3 | 1527 | agacgtcctggaggaagtcc | 0 | 70 |
| 126011 | Coding | 3 | 1550 | ctgaaggctcttggtggagg | 55 | 71 |
| 126012 | Coding | 3 | 1622 | ggccacaacttcaacaggct | 19 | 72 |
| 126013 | Coding | 3 | 1689 | tgataccttcctccttgacc | 36 | 73 |
| 126014 | Coding | 3 | 1756 | agtccagaatcaggatccac | 54 | 74 |
| 126015 | Coding | 3 | 1793 | cttcccacctttctccagga | 50 | 75 |
| 126016 | Coding | 3 | 1827 | cgatgtccaccaggccaagg | 49 | 76 |
| 126017 | Coding | 3 | 1876 | ttgtcgtcctccagaagctg | 51 | 77 |
| 126018 | Coding | 3 | 1907 | ccaggacctgaatatccaat | 0 | 78 |
| 126019 | Coding | 3 | 1970 | ggcatcctccttggacggca | 31 | 79 |
| 126020 | Coding | 3 | 2027 | tttggagtgccaagcgttcc | 45 | 80 |
| 126021 | Coding | 3 | 2081 | ctggccatagtcaatctcca | 53 | 81 |
| 126022 | Coding | 3 | 2108 | tgtgagcttcttcactgcct | 68 | 82 |
| 126023 | Coding | 3 | 2185 | atactttccacatcaaagat | 52 | 83 |
| 126024 | Coding | 3 | 2212 | atctcatactccaccatggc | 57 | 84 |
| 126025 | Coding | 3 | 2269 | tatgcggcctggatctgcct | 34 | 85 |
| 126026 | Coding | 3 | 2331 | ccaggatctgagagtcgctg | 5 | 86 |
| 126027 | Coding | 3 | 2395 | aggagcggaggcttcttcat | 50 | 87 |
| 126028 | Coding | 3 | 2464 | taggccacctcgatgtccag | 15 | 88 |
| 126029 | Coding | 3 | 2512 | tcgatgggatccttgctgct | 0 | 89 |
| 126030 | Coding | 3 | 2553 | caaccaccttaatgtcagtt | 63 | 90 |
| 126031 | Coding | 3 | 2567 | ttcagaatctctgtcaacca | 74 | 91 |
| 126032 | Coding | 3 | 2603 | agtgttcttaacatacttcc | 69 | 92 |
| 126033 | Coding | 3 | 2675 | gcattcgccttcacgctcta | 69 | 93 |
| 126034 | Coding | 3 | 2750 | agcaaagttggtggtcctgg | 39 | 94 |
| 126035 | Coding | 3 | 2808 | tgtagcctgtcacgggcgct | 21 | 95 |
| 126036 | Coding | 3 | 2845 | gagaccatgtcagcgaaata | 49 | 96 |
| 126037 | Coding | 3 | 2913 | caacttctcccaacaggatt | 68 | 97 |
| 126038 | Coding | 3 | 2941 | tgcttcagttcatacatgtt | 68 | 98 |
| 126539 | Coding | 3 | 2980 | ctgtgcttgcccttgggtaa | 23 | 99 |
| 126040 | Coding | 3 | 2994 | ccaaacctttgacactgtgc | 75 | 100 |
| 126041 | Coding | 3 | 3030 | gactaatgttagctgaagga | 13 | 101 |
| 126042 | Coding | 3 | 3180 | acagggaggtcttaaaattg | 47 | 102 |
| 126043 | 3'UTR | 3 | 3214 | accgggtgtgactcggctac | 39 | 103 |
| 126044 | 3'UTR | 3 | 3228 | ttcataccacagccaccggg | 0 | 104 |

As shown in Table 1, SEQ ID NOs 25, 26, 28, 29, 30, 32, 37, 38, 39, 40, 41, 42, 43, 45, 48, 51, 52, 53, 54, 57, 58, 59, 60, 61, 63, 65, 66, 67, 68, 71, 73, 74, 77, 79, 80, 81, 82, 83, 84, 85, 87, 90, 91, 92, 93, 97, 98, 100, 102 and 103 demonstrated at least 25% inhibition of human PARP-1 expression in this assay and are therfore preferred.

Example 16

Antisense Inhibition of Human PARP-2 Expression by Chimeric Phosphorothioate Oligonucleotides having 2'-MOE Wings and a Dexoy Gap In accordance with the present invention, a series of oligonucleotides were designed to target different regions of the human PARP-2 RNA, using published sequences (GenBank accession number AF085734, incorporated herein as SEQ ID NO: 7, and GenBank accession number AJ236876, incorporated herein as SEQ ID NO: 105). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-cleotides, which is flanked on both sides (5' and 3' directions) by five-nucleotide "wings". The wings are compoed of 2'-methoxyethyl (2'-MOE)nucleotides. The internucleoside (backbone) linkages are phosphorothioate (P=S) throughout the oligonucleotide. All cytidine residues are 5-ethylcytidines. The compounds were analyzed for their effect on human PARP-2 mRNA levels by quantitative real-time PCR as described in other examples herein. Data are averages from two experiments. If present, "N.D." indicates "no data".

TABLE 2

Inhibition of human PARP-2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 126125 | 5'UTR | 7 | 2 | tcagcggccgctgaattcta | 0 | 106 |
| 126126 | 5'UTR | 7 | 58 | ttaatgctctcgccctgccg | 11 | 107 |
| 126127 | 5'UTR | 7 | 85 | tgccattattaactcttttg | 38 | 108 |
| 126128 | 5'UTR | 7 | 89 | gtgttgccattattaactct | 60 | 109 |
| 126129 | 5'UTR | 7 | 148 | tcgactcctgtctctggcat | 93 | 110 |
| 126130 | Coding | 7 | 194 | tctgtcctgtccttattagc | 23 | 111 |
| 126131 | Coding | 7 | 216 | tggcataccatcttgcttgt | 70 | 112 |
| 126132 | Coding | 7 | 233 | ctggcccatgaccttcctgg | 34 | 113 |
| 126133 | Coding | 7 | 256 | tcacagattcagagaccctt | 0 | 114 |
| 126134 | Coding | 7 | 271 | ttaacagcaaggccttcaca | 57 | 115 |
| 126135 | Coding | 7 | 297 | ctctgggtccacaggagctt | 54 | 116 |
| 126136 | Coding | 7 | 311 | accttggctgtacactctgg | 81 | 117 |
| 126137 | Coding | 7 | 333 | acaatacacatgagccttcc | 37 | 118 |
| 126138 | Coding | 7 | 359 | atgacatcatagacatcatt | 58 | 119 |
| 126139 | Coding | 7 | 379 | ggagattggtctgatttagc | 32 | 120 |
| 126140 | Coding | 7 | 402 | atagtacttgttgttgttga | 75 | 121 |
| 126141 | Coding | 7 | 447 | aacactgaagttcctctggg | 57 | 122 |
| 126142 | Coding | 7 | 492 | caggctgtgctgtcccattt | 24 | 123 |
| 126143 | Coding | 7 | 507 | gcctgaacaagccaccaggc | 50 | 124 |
| 126144 | Coding | 7 | 523 | tggccttgttgagattgcct | 0 | 125 |
| 126145 | Coding | 105 | 578 | tctttgtttcctcttcatcc | 63 | 126 |
| 126146 | Coding | 7 | 581 | tctcgatcttcccaattgtt | 72 | 127 |
| 126147 | Coding | 105 | 593 | taagagattcctctttcttt | 45 | 128 |
| 126148 | Coding | 7 | 605 | tttccaggcaccttctcaaa | 66 | 129 |
| 126149 | Coding | 7 | 624 | catctgtagcatatcatatt | 69 | 130 |
| 126150 | Coding | 7 | 641 | gtattggtggcatagtccat | 10 | 131 |
| 126151 | Coding | 7 | 708 | tagctgtgactctggcttca | 75 | 132 |
| 126152 | Coding | 7 | 732 | tattaactcctgtacccgaa | 79 | 133 |
| 126153 | Coding | 7 | 752 | tgaacattacagatcaactt | 48 | 134 |
| 126154 | Coding | 7 | 837 | tgccttgatttgtgccactg | 56 | 135 |
| 126155 | Coding | 105 | 848 | ggatcctggtgtagaattca | 32 | 136 |
| 126156 | Coding | 7 | 859 | tcttcttaagagactggtaa | 67 | 137 |
| 126157 | Coding | 105 | 865 | gagtccaaagtcatgcggga | 37 | 138 |
| 126158 | Coding | 7 | 875 | cgaatacaatcctcaatctt | 6 | 139 |
| 126159 | Coding | 7 | 894 | tcgtccatgctggccagccc | 42 | 140 |
| 126160 | Coding | 7 | 912 | gcatgcttccatgagagctc | 28 | 141 |
| 126161 | Coding | 7 | 931 | tcctggtgtagaattcattg | 62 | 142 |
| 126162 | Coding | 7 | 935 | ggaatcctggtgtagaattc | 34 | 143 |
| 126163 | Coding | 7 | 974 | gtccggattagtggaggagt | 11 | 144 |
| 126164 | Coding | 7 | 993 | ttctgacagttccttctgtg | 24 | 145 |
| 126165 | Coding | 7 | 1049 | ttcaccagcttaatagcaat | 48 | 146 |
| 126166 | Coding | 105 | 1052 | cataactttcatggtcaagg | 61 | 147 |
| 126167 | Coding | 105 | 1069 | ggaaatcactttgaactcat | 68 | 148 |
| 126168 | Coding | 7 | 1094 | ctatagtgttggtccaatgg | 63 | 149 |
| 126169 | Coding | 7 | 1114 | gcaaggcacaatgtaggttt | 49 | 150 |
| 126170 | Coding | 7 | 1139 | tcgtaactttcatggtcaag | 70 | 151 |
| 126171 | Coding | 7 | 1147 | ctttgaactcgtaactttca | 68 | 152 |
| 126172 | Coding | 7 | 1155 | ggaaatcactttgaactcgt | 80 | 153 |
| 126173 | Coding | 7 | 1167 | ttgtaggtactgggaaatca | 45 | 154 |
| 126174 | Coding | 7 | 1181 | ggagcatgggtagattgtag | 55 | 155 |

TABLE 2-continued

Inhibition of human PARP-2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 126175 | Coding | 7 | 1211 | agcaaggtcatggtatagtc | 17 | 156 |
| 126176 | Coding | 7 | 1239 | accatccttctccacttcaa | 60 | 157 |
| 126177 | Coding | 7 | 1254 | gaaggcttctttctcaccat | 45 | 158 |
| 126178 | Coding | 7 | 1278 | catcctgttatgaaggtcct | 82 | 159 |
| 126179 | Coding | 105 | 1279 | tgtgatgggagcttcaggtg | 32 | 160 |
| 126180 | Coding | 7 | 1293 | accatgccatagaagcatcc | 29 | 161 |
| 126181 | Coding | 7 | 1312 | cccagttactcatcctggaa | 57 | 162 |
| 126182 | Coding | 7 | 1331 | ccatggctcaagattcccac | 56 | 163 |
| 126183 | Coding | 7 | 1347 | gtgggcaattcgaagcccat | 48 | 164 |
| 126184 | Coding | 7 | 1398 | agcaaagtagattcctttcc | 0 | 165 |
| 126185 | Coding | 7 | 1413 | cttggaagacatgtcagcaa | 55 | 166 |
| 126186 | Coding | 7 | 1433 | gcaaagcagtaattggcact | 0 | 167 |
| 126187 | Coding | 7 | 1449 | attctttaggcgagaggcaa | 39 | 168 |
| 126188 | Coding | 7 | 1463 | agcagcagtcctgtattctt | 60 | 169 |
| 126189 | Coding | 7 | 1485 | acctagagctacctctgata | 34 | 170 |
| 126190 | Coding | 7 | 1503 | tagtagttcattacactgac | 27 | 171 |
| 126191 | Coding | 7 | 1515 | aggattggcctctagtagtt | 0 | 172 |
| 126192 | Coding | 7 | 1532 | agcaatccttcggccttagg | 69 | 173 |
| 126193 | Coding | 7 | 1575 | gggagccatcttgcccagcc | 20 | 174 |
| 126194 | Coding | 7 | 1607 | ctcccattcagggtgacgaa | 20 | 175 |
| 126195 | Coding | 7 | 1625 | ggtcctaatggcactgtact | 15 | 176 |
| 126196 | Coding | 7 | 1647 | cagaattcctgtgtcacttg | 42 | 177 |
| 126197 | Coding | 7 | 1672 | agttgagggtataaccatct | 72 | 178 |
| 126198 | Stop Codon | 105 | 1682 | atatcaacattcaccacagc | 53 | 179 |
| 126199 | 3'UTR | 105 | 1699 | gatctctggtttatttaata | 62 | 180 |
| 126200 | Coding | 7 | 1726 | ttaaaaggtaccgcatacgg | 57 | 181 |
| 126201 | Stop Codon | 7 | 1768 | agatcaacattcaccacagc | 62 | 182 |
| 126202 | 3'UTR | 7 | 1795 | ttgaagatcagatctctggt | 0 | 183 |
| 126203 | 3'UTR | 7 | 1822 | caagtacaacactgcttatt | 0 | 184 |
| 126204 | 3'UTR | 7 | 1848 | tattacataaaatatcacaa | 42 | 185 |

As shown in Table 2, SEQ ID NOs 108, 109, 110, 112, 113, 115, 116, 117, 118, 119, 120, 121, 122, 124, 126, 127, 128, 129, 130, 132, 133, 134, 135, 136, 137, 138, 140, 141, 142, 143, 146, 147, 148, 149, 150, 151, 152, 153, 154, 155, 157, 158, 159, 160, 161, 162, 163, 164, 166, 168, 169, 170, 171, 173, 177, 178, 179, 180, 181, 182 and 185 demonstrated at least 25% inhibition of human PARP-2 expression in this assay and are therefore preferred.

Example 17

Antisense Inhibition of Mouse PARP-2 Expression by Chimeric Phosphorothioate Oligonucleotides having 2'-MOE Wings and a Deoxy Gap.

In accordance with the present invention, a second series of oligonucleotides were designed to target different regions of the mouse PARP-2 RNA, using published sequences (GenBank accession number AF072521, incorporated herein as SEQ ID NO: 18). The oligonucleotides are shown in Table 3. "Target site" indicates the first (5'-most) nucleotide number on the particular target sequence to which the oligonucleotide binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse PARP-2 mRNA levels by quantitative real-time PCR as described in other examples herein. Data are averages from two experiments. If present, "N.D." indicates "no data".

TABLE 3

Inhibition of mouse PARP-2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 110231 | 5'UTR | 18 | 1 | gcactcgccttccagagcct | 62 | 186 |
| 110232 | 5'UTR | 18 | 9 | ttcatttagcactcgccttc | 24 | 187 |
| 110233 | 5'UTR | 18 | 27 | attatcaactttcttggctt | 42 | 188 |
| 110234 | 5'UTR | 18 | 43 | ctgttgctttgttgccatta | 31 | 189 |
| 110235 | 5'UTR | 18 | 55 | gagagtcgtcttctgttgct | 57 | 190 |

TABLE 3-continued

Inhibition of mouse PARP-2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 110236 | Start Codon | 18 | 69 | cttcttgccaggaggagagt | 29 | 191 |
| 110237 | Start Codon | 18 | 82 | ggcacgtgcgcatcttcttg | 0 | 192 |
| 110238 | Coding | 18 | 110 | ttccctccagccataggccc | 28 | 193 |
| 110239 | Coding | 18 | 139 | ctcgattgtcttttgtcctg | 62 | 194 |
| 110240 | Coding | 18 | 153 | ggtcttcacagagtctcgat | 57 | 195 |
| 110241 | Coding | 18 | 166 | cctttaacagcaaggtcttc | 23 | 196 |
| 110242 | Coding | 18 | 209 | tttcccagcttggctgcaca | 17 | 197 |
| 110243 | Coding | 18 | 234 | atctccttcacaatacacat | 16 | 198 |
| 110244 | Coding | 18 | 258 | atttagcatgacatcataga | 0 | 199 |
| 110245 | Coding | 18 | 283 | tgttgttgaactggagattg | 28 | 200 |
| 110246 | Coding | 18 | 305 | agctgaataaggtagtactt | 30 | 201 |
| 110247 | Coding | 18 | 328 | tcctctgggcatcatcttct | 29 | 202 |
| 110248 | Coding | 18 | 350 | cacctcatccaaacactgaa | 32 | 203 |
| 110249 | Coding | 18 | 373 | gccccgtctttccaactcgg | 47 | 204 |
| 110250 | Coding | 18 | 396 | agaacaagtcaccaagctgt | 58 | 205 |
| 110251 | Coding | 18 | 418 | cttttgctttgttgaggtca | 72 | 206 |
| 110252 | Coding | 18 | 474 | ctcacggtcctcccaattgt | 42 | 207 |
| 110253 | Coding | 18 | 512 | tgtaacatgtcgtatttcc | 55 | 208 |
| 110254 | Coding | 18 | 534 | cgtgctggcagcatagtcca | 57 | 209 |
| 110255 | Coding | 18 | 557 | tcttttgttttactttcatc | 0 | 210 |
| 110256 | Coding | 18 | 580 | actcaggcttcaaagtttcc | 35 | 211 |
| 110257 | Coding | 18 | 603 | ctggactcgaagatccagct | 42 | 212 |
| 110258 | Coding | 18 | 624 | acagatcaactttagcagct | 60 | 213 |
| 110259 | Coding | 18 | 647 | atttcttccatggtctgcac | 59 | 214 |
| 110260 | Coding | 18 | 669 | gtcatacttcatctcaatca | 48 | 215 |
| 112061 | Coding | 18 | 709 | tttgcgccactgtcagcttt | 76 | 216 |
| 112062 | Coding | 18 | 732 | gagagactggtaaccggcct | 72 | 217 |
| 112063 | Coding | 18 | 754 | ggatgcagtcctcaatcttc | 39 | 218 |
| 110264 | Coding | 18 | 775 | ctcgcccatgctggccagcg | 56 | 219 |
| 110265 | Coding | 18 | 795 | attgcacgcttcaacaagcg | 53 | 220 |
| 110266 | Coding | 18 | 816 | agggatcctggtgtagaatt | 9 | 221 |
| 110267 | Coding | 18 | 836 | atggagagtccaaagtcatg | 28 | 222 |
| 110268 | Coding | 18 | 856 | ctgtccggattactggaggg | 22 | 223 |
| 110269 | Coding | 18 | 875 | ttgtctgacagttccttctc | 20 | 224 |
| 110270 | Coding | 18 | 892 | cctctagcagttttactttg | 36 | 225 |
| 110271 | Coding | 18 | 912 | aatttcaatgtctcccaatg | 16 | 226 |
| 110272 | Coding | 18 | 932 | gacttcaccagtttaagggc | 56 | 227 |
| 110273 | Coding | 18 | 952 | gttctaggccttggcgctct | 41 | 228 |
| 110274 | Coding | 18 | 972 | atagtgttggtccagtgggt | 30 | 229 |
| 110275 | Coding | 18 | 993 | caaagcacagtgtaggtttc | 35 | 230 |
| 110276 | Coding | 18 | 1013 | ctttcatggtccagaggacg | 3 | 231 |
| 110277 | Coding | 18 | 1033 | aaatcaccttaaactcatta | 32 | 232 |
| 110278 | Coding | 18 | 1053 | cgtagactgtaggtactgag | 65 | 233 |
| 110279 | Coding | 18 | 1074 | gtccttgtgtgtaggagcat | 64 | 234 |
| 110280 | Coding | 18 | 1095 | atccagcaaggtcatagtat | 49 | 235 |
| 110281 | Coding | 18 | 1115 | tccttctctacttcgaaaac | 26 | 236 |
| 110282 | Coding | 18 | 1135 | tgaaggcctctttctccct | 51 | 237 |
| 110283 | Coding | 18 | 1155 | cctgttaggaaggtcctccc | 48 | 238 |
| 110284 | Coding | 18 | 1174 | atccatgccagagcagcatc | 6 | 239 |
| 110285 | Coding | 18 | 1191 | ccagttactcagcctggatc | 38 | 240 |
| 110286 | Coding | 18 | 1211 | ccgtggctcaggatccccac | 38 | 241 |
| 110287 | Coding | 18 | 1247 | cctgtgatgggagcctcagg | 22 | 242 |
| 110288 | Coding | 18 | 1266 | tccttttccaaacatataac | 8 | 243 |
| 110289 | Coding | 18 | 1286 | gacatgtcagcaaagtagat | 42 | 244 |
| 110290 | Coding | 18 | 1307 | cagtaattggcactcttgga | 69 | 245 |
| 110291 | Coding | 18 | 1328 | ttctttaggcgagaggcaaa | 0 | 246 |
| 119292 | Coding | 18 | 1347 | cagaagaagcaatcctgtat | 15 | 247 |
| 110293 | Coding | 18 | 1367 | tgacctagagctacctctga | 42 | 248 |
| 110294 | Coding | 18 | 1387 | cctccagtagttcattacac | 26 | 249 |
| 110295 | Coding | 18 | 1405 | cttgtgcttaggattggcc | 45 | 250 |
| 110296 | Coding | 18 | 1423 | gcttgccccgaagcaatcct | 43 | 251 |
| 110297 | Coding | 18 | 1443 | tcccatcccttggtgctat | 60 | 252 |
| 110298 | Coding | 18 | 1463 | gcagggctgggagccatctt | 17 | 253 |
| 110299 | Coding | 18 | 1481 | ttcagggtgatgaagtgggc | 0 | 254 |
| 110300 | Coding | 18 | 1499 | aagggcactgtactcccatt | 59 | 255 |
| 110301 | Coding | 18 | 1517 | gtgtcacttgctggtcctaa | 24 | 256 |
| 110302 | Coding | 18 | 1537 | cctctggattgagaattcct | 50 | 257 |
| 110303 | Coding | 18 | 1556 | ttgtagttgagggtgtaccc | 2 | 258 |
| 110304 | Coding | 18 | 1577 | gggctataaacaataaactc | 38 | 259 |
| 110305 | Coding | 18 | 1613 | tgaatctttagaaggtatcg | 54 | 260 |
| 110306 | Coding | 18 | 1633 | atagctgcaggaagttaaat | 45 | 261 |

TABLE 3-continued

Inhibition of mouse PARP-2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 110307 | Stop Codon | 18 | 1651 | gtctgatcaacattcaccat | 69 | 262 |
| 110308 | 3'UTR | 18 | 1670 | attatattctctctggcttg | 67 | 263 |
| 110309 | 3'UTR | 18 | 1705 | caagaaccataatattgctt | 0 | 264 |
| 110310 | 3'UTR | 18 | 1740 | ttatactattttattaaaca | 0 | 265 |

As shown in Table 3, SEQ ID NOs 186, 188, 189, 190, 191, 193, 194, 195, 200, 201, 202, 203, 204, 205, 206, 207, 208, 209, 211, 212, 213, 214, 215, 216, 217, 218, 219, 220, 222, 225, 227, 228, 229, 230, 232, 233, 234, 235, 236, 237, 238, 240, 241, 244, 245, 248, 249, 250, 251, 252, 255, 257, 259, 260, 261, 262 and 263 demonstrated at least 25% inhibition of mouse PARP-2 expression in this experiment and are therefore preferred.

Example 18

Antisnse Inhibition of Human PARP-3 Expression by Chimeric Phosphorothioate Oligonucleotides having 2'-MOE Wings and a Deoxy Gap In accordance with the present invention, a series of oligonuleotides were designed to target different regions of the human PARP-3 RNA, using published sequences (GenBank accession number AF083068, incorporated herein as SEQ ID NO: 11) The oligonucleotides are shown in Table 4. "Target site" indicates the first (5'-most) nucleotide number on the particular target sequence to which the oligonucleotide binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human PARP-3 mRNA levels by quantitative real-time PCR as described in other examples herein. Data are averages from two experiments. If present, "N.D." indicates "no data".

TABLE 4

Inhibition of human PARP-3 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 126045 | 5'UTR | 11 | 3 | aggcgtgaattagggagaga | 5 | 266 |
| 126046 | 5'UTR | 11 | 11 | tgagcctcaggcgtgaatta | 1 | 267 |
| 126047 | 5'UTR | 11 | 27 | gtctagcaactctccatgag | 21 | 268 |
| 126048 | 5'UTR | 11 | 75 | ctggctgccacccggcctgg | 5 | 269 |
| 126049 | 5'UTR | 11 | 89 | acatgggagaggtcctggct | 2 | 270 |
| 126050 | Start Codon | 11 | 118 | gagccatggctgtcccaaga | 0 | 271 |
| 126051 | Coding | 11 | 140 | tgtacccagggcttcggctt | 11 | 272 |
| 126052 | Coding | 11 | 154 | cagggccctcagtctgtacc | 0 | 273 |
| 126053 | Coding | 11 | 181 | ttcctgcctgccggcccttc | 42 | 274 |
| 126054 | Coding | 11 | 213 | ctcagcggtggagcggaagg | 0 | 275 |
| 126055 | Coding | 11 | 236 | tctgcgggtatggccttgag | 41 | 276 |
| 126056 | Coding | 11 | 249 | gattatgcgcttctctgcgg | 56 | 277 |
| 126057 | Coding | 11 | 272 | agtggacatgttggatccac | 16 | 278 |
| 126058 | Coding | 11 | 309 | gtagtcctcatacacctggg | 6 | 279 |
| 126059 | Coding | 11 | 337 | cgatgttggtctggttcagg | 0 | 280 |
| 126060 | Coding | 11 | 350 | ttgttgttgttctcgatgtt | 7 | 281 |
| 126061 | Coding | 11 | 368 | tggatgatgtagaacttctt | 26 | 282 |
| 126062 | Coding | 11 | 391 | agcggttgctgtcttggagc | 24 | 283 |
| 126063 | Coding | 11 | 416 | ccccagcggttccagcaggt | 0 | 284 |
| 126064 | Coding | 11 | 434 | ccgacctctcccacacggcc | 45 | 285 |
| 126065 | Coding | 11 | 442 | ttgactggccgacctctccc | 44 | 286 |
| 126066 | Coding | 11 | 454 | agtggttgatctttgactgg | 0 | 287 |
| 126067 | Coding | 11 | 464 | agccttgtgaagtggttgat | 31 | 288 |
| 126068 | Coding | 11 | 489 | ctcaaagtccttctttgcat | 0 | 289 |

TABLE 4-continued

Inhibition of human PARP-3 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 126069 | Coding | 11 | 506 | ttttcccgaaatttcttctc | 67 | 290 |
| 126070 | Coding | 11 | 531 | ccgctctgcccagttgttct | 5 | 291 |
| 126071 | Coding | 11 | 558 | cttgcccgggtgagacacaa | 35 | 292 |
| 126072 | Coding | 11 | 574 | cttcgataagtgtgtacttg | 0 | 293 |
| 126073 | Coding | 11 | 594 | ggcctcatcctctgcctgta | 36 | 294 |
| 126074 | Coding | 11 | 621 | tctgtccaccttcaccacag | 0 | 295 |
| 126075 | Coding | 11 | 644 | ttagtcacagtcctcactgg | 7 | 296 |
| 126076 | Coding | 11 | 662 | gagcagggctgcacccgctt | 41 | 297 |
| 126077 | Coding | 11 | 683 | ttctgcgtggctgggtccag | 76 | 298 |
| 126078 | Coding | 11 | 697 | tgttagtgatgagcttctgc | 54 | 299 |
| 126079 | Coding | 11 | 720 | cttgaacatctccttgctga | 47 | 300 |
| 127080 | Coding | 11 | 732 | ggccatggtgttcttgaaca | 19 | 301 |
| 126081 | Coding | 11 | 755 | ttcttcacatccaggtccat | 72 | 302 |
| 127082 | Coding | 11 | 782 | tgcttgctcagctttcccag | 58 | 303 |
| 126083 | Coding | 11 | 800 | aaaccccgtgcaatctgttg | 0 | 304 |
| 126084 | Coding | 11 | 823 | cctccagcgcctccaaggcc | 27 | 305 |
| 126085 | Coding | 11 | 838 | ggcctttcagggcctcctcc | 39 | 306 |
| 126086 | Coding | 11 | 858 | gctttggccaccatccgtgg | 31 | 307 |
| 126087 | Coding | 11 | 881 | aagtgtgaggacagctcctc | 58 | 308 |
| 126088 | Coding | 11 | 902 | ttgtgcgggatgacggtgta | 31 | 309 |
| 126089 | Coding | 11 | 914 | ctgtggccgaagttgtgcgg | 0 | 310 |
| 126090 | Coding | 11 | 956 | ttggcctgcagaagctcagg | 10 | 311 |
| 126091 | Coding | 11 | 980 | gccagcaccagcagcatgtc | 24 | 312 |
| 126092 | Coding | 11 | 996 | ggccagctcgatgtccgcca | 0 | 313 |
| 126093 | Coding | 11 | 1034 | accgtcttctcctgctcaga | 25 | 314 |
| 126094 | Coding | 11 | 1048 | gtggcacctcctccaccgtc | 11 | 315 |
| 126095 | Coding | 11 | 1072 | gctggtagtctcggtccagg | 0 | 316 |
| 126096 | Coding | 11 | 1099 | ctagcagctgcagctggcac | 15 | 317 |
| 126097 | Coding | 11 | 1115 | tcaggtgctccagagtctag | 14 | 318 |
| 126098 | Coding | 11 | 1129 | gtatcaccttgtactcaggt | 26 | 319 |
| 126099 | Coding | 11 | 1152 | gccagtctgttctaagtagg | 28 | 320 |
| 126100 | Coding | 11 | 1169 | gggcacctgtggttgctgcc | 46 | 321 |
| 126101 | Coding | 11 | 1189 | tccagatgtgttgaagtgta | 51 | 322 |
| 126102 | Coding | 11 | 1221 | gaatctgtcttcctcccctt | 31 | 323 |
| 126103 | Coding | 11 | 1248 | ccgattacccagtttggagt | 3 | 324 |
| 126104 | Coding | 11 | 1276 | ccatgttggtgccatgccac | 0 | 325 |
| 126105 | Coding | 11 | 1304 | ccactagtgaggatggcggc | 32 | 326 |
| 126106 | Coding | 11 | 1331 | ccaccagaatgtggcatgat | 21 | 327 |
| 126107 | Coding | 11 | 1362 | tgaggcaaagtagatgccct | 28 | 328 |
| 126108 | Coding | 11 | 1328 | catgccaataacatatccag | 32 | 329 |
| 126109 | Coding | 11 | 1427 | atgtagccgacatggtgggc | 49 | 330 |
| 126110 | Coding | 11 | 1465 | tatggtgctctctgcccagg | 17 | 331 |
| 126111 | Coding | 11 | 1480 | ggttgtccgtgttgatatgg | 35 | 332 |
| 126112 | Coding | 11 | 1501 | gaggtgggctcttcaagctg | 0 | 333 |
| 126113 | Coding | 11 | 1532 | tggcctcgggcaatgacact | 0 | 334 |
| 126114 | Coding | 11 | 1566 | caactcagtgtcctgggtcg | 0 | 335 |
| 126115 | Coding | 11 | 1595 | ggcaccaccacttgctggcc | 48 | 336 |
| 126116 | Coding | 11 | 1617 | gcagggcacaggctggccct | 0 | 337 |
| 126117 | Coding | 11 | 1632 | gctgctgaactctgggcagg | 21 | 338 |
| 126118 | Coding | 11 | 1664 | tagatgaggtactcgctctg | 3 | 339 |
| 126119 | Coding | 11 | 1694 | aggtagcgcaggcgacactg | 24 | 340 |
| 126120 | Stop Codon | 11 | 1717 | gcactcagaggtggacctcc | 50 | 341 |
| 126121 | 3'UTR | 11 | 1749 | ccagccttgcaggacccccgg | 65 | 342 |
| 126122 | 3'UTR | 11 | 1767 | atgattgaagatcacagtcc | 64 | 343 |
| 126123 | 3'UTR | 11 | 1783 | accagagatgggcaggatga | 24 | 344 |
| 126124 | 3'UTR | 11 | 1824 | caacgtattgtattcttgaa | 52 | 345 |

As shown in Table 4, SEQ ID NOs 274, 276, 277, 282, 285, 286, 288, 290, 292, 294, 297, 298, 299, 300, 302, 303, 305, 306, 307, 308, 309, 319, 320, 321, 322, 323, 326, 328, 329, 330, 332, 336, 341, 342, 343 and 345 demonstrated at least 25% inhibition of human PARP-3 expression in this assay and are therefore preferred.

Example 19

Western Blot Analysis of PARP Protein Levels

Western blot analysis (immunoblot analysis) is carried out using standard methods. Cells are harvested 16–20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to PARP is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. An antisense compound 18 to 30 nucleobases in length targeted to nucleobases 184 through 3199 of a coding region of a nucleic acid molecule encoding human PARP of SEQ ID NO:3, nucleobases 58 through 167 of a 5'- untranslated region, or nucleobases 194 through 1691 of a coding region of a nucleic acid molecule encoding human PARP of SEQ ID NO:7, or nucleobases 1749-1843 of a 3'-untranslated region of a nucleic acid molecule encoding human PARP of SEO ID NO: 11, or nucelobases 1-74 of a 5'-untranslated region, nucleobases 110 through 1652 of a coding region, or nucleobases 1670 through 1689 of a 3'- untranslated region of a nucleic acid molecule encoding mouse PARP of SEQ ID NO:18, wherein said antisense compound specifically hybridizes with one of said regions and inhibits the expression of said human or mouse PARP nucleic acid molecules.

2. The antisense compound of claim 1 which is an antisense oligonucleotide.

3. An antisense compound up to 30 nucleobases in length comprising at least 18 consecutive nucleobases of SEQ ID NO: 25, 26, 28, 29, 30, 32, 34, 36, 37, 38, 39, 40, 41, 42, 43, 45, 48, 51, 52, 53, 54, 55, 56, 57, 58, 59, 60, 61, 63, 65, 66, 67, 68, 71, 73, 74, 75, 76, 77, 79, 80, 81, 82, 83, 84, 85, 87, 90, 91, 92, 93, 94, 96, 97, 98, 100, 102, 103, 108, 109, 110, 112, 113, 115, 116, 117, 118, 119, 120, 121, 122, 124, 126, 127, 128, 129, 130, 132, 133, 134, 135, 136, 137, 138, 140, 141, 142, 143, 146, 147, 148, 149, 150, 151, 152, 153, 154, 155, 157, 158, 159, 160, 161, 162, 163, 164, 166, 168, 169, 170, 171, 173, 177, 178, 179, 180, 181, 182, 185, 274, 276, 277, 282, 285, 286, 288, 290, 292, 294, 297, 298, 299, 300, 302, 303, 305, 306, 307, 308, 309, 319, 320, 321, 322, 323, 326, 328, 329, 330, 332, 336, 341, 342, 343 or 345 which inhibits the expression of human or mouse PARP.

4. The antisense compound of claim 2 wherein the antisense oligonucleotide comprises at least one modified internucleoside linkage.

5. The antisense compound of claim 4 wherein the modified internucleoside linkage is a phosphorothioate linkage.

6. The antisense compound of claim 2 wherein the antisense oligonucleotide comprises at least one modified sugar moiety.

7. The antisense compound of claim 6 wherein the modified sugar moiety is a 2'-O-methoxyethyl sugar moiety.

8. The antisense compound of claim 2 wherein the antisense oligonucleotide comprises at least one modified nucleobase.

9. The antisense compound of claim 8 wherein the modified nucleobase is a 5-methylcytosine.

10. The antisense compound of claim 1 wherein the antisense oligonucleotide is a chimeric oligonucleotide.

11. A composition comprising the antisense compound of claim 1 and a pharmaceutically acceptable carrier or diluent.

12. The composition of claim 11 further comprising a colloidal dispersion system.

13. The composition of claim 11 wherein the antisense compound is an antisense oligonucleotide.

14. A method of inhibiting the expression of human or mouse PARP in cells or tissues comprising contacting said cells or tissues in vitro with the antisense compound of claim 1 so that expression of human or mouse PARP is inhibited.

15. The antisense compound of claim 3 which is an antisense oligonucleotide.

16. The antisense compound of claim 15 wherein the antisense oligonucleotide comprises at least one modified internucleoside linkage.

17. The antisense compound of claim 16 wherein the modified internucleoside linkage is a phosphorothioate linkage.

18. The antisense compound of claim 15 wherein the antisense oligonucleotide comprises at least one modified sugar moiety.

19. The antisense compound of claim 18 wherein the modified sugar moiety is a 2'-O-methoxyethyl sugar moiety.

20. The antisense compound of claim 15 wherein the antisense oligonucleotide comprises at least one modified nucleobase.

21. The antisense compound of claim 20 wherein the modified nucleobase is a 5-methylcytosine.

22. The antisense compound of claim 15 wherein the antisense oligonucleotide is a chimeric oligonucleotide.

23. A composition comprising the antisense compound of claim 3 and a pharmaceutically acceptable carrier or diluent.

24. The composition of claim 23 further comprising a colloidal dispersion system.

25. The composition of claim 23 wherein the antisense compound is an antisense oligonucleotide.

26. A method of inhibiting the expression of human or mouse PARP in cells or tissues comprising contacting said cells or tissues in vitro with the antisense compound of claim 3 so that expression of human or mouse PARP is inhibited.

* * * * *